(12) United States Patent
Gabor et al.

(10) Patent No.: US 10,544,469 B2
(45) Date of Patent: Jan. 28, 2020

(54) METHODS AND COMPOSITIONS FOR PRODUCING CAPSICUM PLANTS WITH POWDERY MILDEW RESISTANCE

(71) Applicant: Seminis Vegetable Seeds, Inc., St. Louis, MO (US)

(72) Inventors: Brad K. Gabor, Woodland, CA (US); Brian J. Just, Ft. Myers, FL (US); Caicheng Huang, Delft (NL); Carl M. Jones, Sacramento, CA (US); Dirk Vreugdenhil, 's-Gravenzande (NL); Joel M. Kniskern, Sacramanto, CA (US); Pablo A. Quijada, Davis, CA (US); Terry Berke, Zamora, CA (US); Anton P. Allersma, Berkel en Rodenrijs (NL); Wenwen Xiang, Davis, CA (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 6 days.

(21) Appl. No.: 15/604,511

(22) Filed: May 24, 2017

(65) Prior Publication Data

US 2017/0362665 A1 Dec. 21, 2017

Related U.S. Application Data

(62) Division of application No. 13/598,496, filed on Aug. 29, 2012, now Pat. No. 9,689,045.

(60) Provisional application No. 61/529,205, filed on Aug. 30, 2011.

(51) Int. Cl.
  *A01H 5/10* (2018.01)
  *C12Q 1/6895* (2018.01)
  *A01H 1/04* (2006.01)
  *A01H 5/08* (2018.01)

(52) U.S. Cl.
  CPC .......... *C12Q 1/6895* (2013.01); *A01H 1/04* (2013.01); *A01H 5/08* (2013.01); *C12Q 2600/156* (2013.01)

(58) Field of Classification Search
  None
  See application file for complete search history.

(56) References Cited

U.S. PATENT DOCUMENTS

| 7,968,773 | B2 | 6/2011 | Van Kan et al. |
| 8,642,845 | B2 † | 2/2014 | Paran |
| 2011/0035832 | A1 † | 2/2011 | Paran |

FOREIGN PATENT DOCUMENTS

| EP | 2247751 | † | 11/2010 |
| WO | WO 2009/098685 A2 | * | 8/2009 |

OTHER PUBLICATIONS

Bai et al, "QTLs for tomato powdery mildew resistance (Oidium lycopersici) in Lycopersicon parviflorum G1, 16-1 co-localize with two qualitative powdery mildew resistance genes," *Mol. Plant Microbe Interact.*; Feb. 2003, vol. 16(2), pp. 169-176.
Murthy et al., *Veg. Sci.*; vol. 24(2); pp. 127-131; 1997.
Reiter et al., "Global and local genome mapping in *Arabidopsis thaliana* by using recombinant inbred lines and random amplified polymorphic DNAs," *Proc. Natl. Acad. Sci.*; Feb. 1992; vol. 89; pp. 1477-1481.
USDA, ARS, National Genetic Resources Program; Germplasm Resources Information Network—(GRIN); National Germplasm Resources Laboratory; Beltsville, MD; IIHR 1238 title, NPGS.
Wu et al., "A COSII genetic map of the pepper genome provides a detailed picture of synteny with tomato and new insights into recent chromosome evolution in the genus *Capsicum*," *Theor. Appl. Genet.*, 2009, vol. 118(7), pp. 1279-1293).
ISA/US; International Search Report and Written Opinion of the International Searching Authority for PCT/US 12/52859, dated Nov. 9, 2012.
Qin et al., "Whole-genome sequencing of cultivated and wild peppers provides insights into *Capsicum* domestication and specialization," *PNAS* 111:5135-5140, 2014.
Sequence Alignments of the marker sequences disclosed in EP 12827559 and US. Publication No. 2011/0035832 with *Capsicum annuum* L. Zunla-1 genomic sequence, available at http://peppersequence.genomics.cn/page/species/blast.jsp, cited Jan. 16, 2018.
Declaration of Nicolas Bardol, dated Jan. 10, 2018.
Syngenta catalog titled, "Poivron 2011," dated Oct. 2010.
Common catalog of varieties of vegetable species, available at http://ec.europa.eu/food/plant/propagation/catalouges/database/public/index.cfm?event=RunSearch, dated on May 5, 2015.
European Commission, "Common catalog of varieties of vegetable species," Official Journal of the European Union, dated Jan. 19, 2010.
Extract of Syngenta catalog, dated 2017.
Reddy et al., "Exploitation of AVRDC's Chili Pepper (*Capsicum* spp.) Germplasm in India," *J. Taiwan Soc. Hort. Sci.* 61(1):1-9, 2015.

(Continued)

*Primary Examiner* — Bratislav Stankovic
(74) *Attorney, Agent, or Firm* — Dentons US LLP; Matthew Madsen

(57) ABSTRACT

The invention relates to pepper plants and lines having resistance to Powdery Mildew, caused by the fungus *Leveillula taurica*. The invention also relates to parts of pepper plants from lines having Powdery Mildew resistance, including seeds capable of growing pepper plants with Powdery Mildew resistance, and fruit. Methods for the identification, use and breeding of Powdery Mildew resistant pepper plants are also provided.

13 Claims, 12 Drawing Sheets

Specification includes a Sequence Listing.

(56) References Cited

OTHER PUBLICATIONS

Third-Party Observation regarding EP 2751289, dated Jan. 25, 2018.
Third party Observations in relation to EP 12827.559.1.†
Marker analysis report.†

\* cited by examiner
† cited by third party

SEQUENCE LISTING

<160> NUMBER OF SEQ ID NOS: 44

<210> SEQ ID NO 1
<211> LENGTH: 121
<212> TYPE: DNA
<213> ORGANISM: Artificial Sequence
<220> FEATURE:
<223> OTHER INFORMATION: Synthetic primer

<400> SEQUENCE: 1
atactaaatc caatagtgct cttccgctga aagttcataa tagcctgtag atttgaaaga      60
rgcaagaggt taatccaaat gaattcgcga tgaaaagcag aataaacgaa acccgggact     120
t                                                                     121

<210> SEQ ID NO 2
<211> LENGTH: 121
<212> TYPE: DNA
<213> ORGANISM: Artificial Sequence
<220> FEATURE:
<223> OTHER INFORMATION: Synthetic primer

<400> SEQUENCE: 2
aataatttat agctccacaa atagtcgata agtggtttag atcaaaaagt tgaaaagtct      60
ytcttacact ttgtgccaag tcaaaggcag tggcggatct acatacaatt caaggggttc     120
a                                                                     121

<210> SEQ ID NO 3
<211> LENGTH: 121
<212> TYPE: DNA
<213> ORGANISM: Artificial Sequence
<220> FEATURE:
<223> OTHER INFORMATION: Synthetic primer

<400> SEQUENCE: 3
aattccatta gaacaggttc catcagagca gcaaaagatt gttcaactat gcaggcagct      60
raataggcct gttatagttg cttcccagtt gctggaatct atgattgaat accctattcc     120
c                                                                     121

<210> SEQ ID NO 4
<211> LENGTH: 107
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (92)..(93)
<223> OTHER INFORMATION: n is a, c, g, or t

<400> SEQUENCE: 4
caatttgcaa gggaaaatcc agcctccatg atgacttatc acaggtcgta aacactgtgt      60
rgtcaatgta gaaactgtaa aaaaaaaaaa anncattaac tagacaa                   107

<210> SEQ ID NO 5
<211> LENGTH: 120
<212> TYPE: DNA
<213> ORGANISM: Artificial Sequence
<220> FEATURE:
<223> OTHER INFORMATION: Synthetic primer

<400> SEQUENCE: 5
gagatcaaat gattcagaca aataaagaat actaaaagaa agtaacatac agtaagagam      60
acatgtgaaa caatgtaaga caattaagag aagggtgaga agcccaccc ctccacgtgc    120

<210> SEQ ID NO 6
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or t

<400> SEQUENCE: 6
tgangtcttt gggtaggaat cctaaataga aatttgtgca gtggagaagt acgtcctgtc    60
raaggaattg ggaagtcact gagtgtcgga caagttgtat gggctccatc tggtgaaggc    120
t    121

<210> SEQ ID NO 7
<211> LENGTH: 121
<212> TYPE: DNA
<213> ORGANISM: Artificial Sequence
<220> FEATURE:
<223> OTHER INFORMATION: Synthetic primer

<400> SEQUENCE: 7
gtaactgacg taagggtaga tccaagattt gaacattatg tattcgagtt agactttcta    60
ktgtagtcca tttggtttat ttatgactcg aaacctatta tttgcactcg tttagtaaac    120
a    121

<210> SEQ ID NO 8
<211> LENGTH: 121
<212> TYPE: DNA
<213> ORGANISM: Artificial Sequence
<220> FEATURE:
<223> OTHER INFORMATION: Synthetic primer

<400> SEQUENCE: 8
cgttccaagt accaactcat ccacacagta cgtacacaca agggcgtgga tgaaaggagc    60
watggctgtg tgttccggga ggaggaagag aaggaggagg taggcgttgc cctgtcgaag    120
g    121

<210> SEQ ID NO 9
<211> LENGTH: 120
<212> TYPE: DNA
<213> ORGANISM: Artificial Sequence
<220> FEATURE:
<223> OTHER INFORMATION: Synthetic primer

<400> SEQUENCE: 9
gccttcggaa atccaaatgt gcctggtgct ggttatggta gcggtcaagc tggtggatcr    60
agaagctcgt ggggttctca gggtccttct ggatatggga acatgggcta tggtaatgca    120

<210> SEQ ID NO 10
<211> LENGTH: 121
<212> TYPE: DNA
<213> ORGANISM: Artificial Sequence
<220> FEATURE:
<223> OTHER INFORMATION: Synthetic primer

<400> SEQUENCE: 10

```
gtggtatggg tggtggaagt taccaggggt atggtgcatc tggtgacaat cccagttctt    60
rtgacagaat ggataccaac agatacatgc agtcacaaaa cactgtaggt ggctatccac   120
c                                                                   121
```

<210> SEQ ID NO 11
<211> LENGTH: 117
<212> TYPE: DNA
<213> ORGANISM: Artificial Sequence
<220> FEATURE:
<223> OTHER INFORMATION: Synthetic primer

<400> SEQUENCE: 11

```
gccatagtta aataggttct ccttctgcta atgtacatca tctatgaaat ttaacatctg    60
yataatgcag gtgcctccta ctttgagatt tgtgatggat ggtgaaatgc ccgatta      117
```

<210> SEQ ID NO 12
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (41)..(41)
<223> OTHER INFORMATION: n is a, c, g, or t

<400> SEQUENCE: 12

```
cacacaaccg atacttacta ttncagaaag tcacttnctt ngcaaccctc cggggaagtt    60
rgtcactttg tcaatcagaa atgcagaatt taaccaagaa taccaagcgg ccgtttcctc   120
a                                                                   121
```

<210> SEQ ID NO 13
<211> LENGTH: 121
<212> TYPE: DNA
<213> ORGANISM: Artificial Sequence
<220> FEATURE:
<223> OTHER INFORMATION: Synthetic primer

<400> SEQUENCE: 13

```
gatataggag tatcatggaa gttgtgccct ttgatatggt atgcgtggaa ccatttgatc    60
yacatttgtc cagtttatgc tctaagtccc agcatatctt agcaatagca gccctgttac   120
a                                                                   121
```

<210> SEQ ID NO 14
<211> LENGTH: 102
<212> TYPE: DNA
<213> ORGANISM: Artificial Sequence
<220> FEATURE:
<223> OTHER INFORMATION: Synthetic primer

<400> SEQUENCE: 14

```
ctattgggaa gcctcccacc aaacatatgt tctatcttac ccaacgttga aagcgtttat    60
ytggcctata ccaattttgc tgggactatt cctcattcca tc                      102
```

```
<210> SEQ ID NO 15
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (26)..(26)
<223> OTHER INFORMATION: n is a, c, g, or t

<400> SEQUENCE: 15
acagaattgg tagccttgat cacccngctt cgggtcctgg tgacatggtg gaacatttgc      60
rgccagaaac tgagtcattt actgaggttt tacttgcaaa gtttgtccga atgctccaga     120
a                                                                    121

<210> SEQ ID NO 16
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (14)..(15)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t

<400> SEQUENCE: 16
tgacctttat agtnnaaaaa aanttaaaan ggacaagaaa tggaaaggga acaaagaaga      60
rtatcagcag cttatctatg tttaacaaat tatgacctcc attagctttt atattaataa     120
a                                                                    121

<210> SEQ ID NO 17
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 17
cgatacatgc gcaccactcg acatcttttg tggttctcaa gataacaatc gcaggtaaca      60
kcatctgtaa atccaataga acaacttggn ggtaataata ttccctnaga acacccaagc     120
a                                                                    121

<210> SEQ ID NO 18
<211> LENGTH: 121
<212> TYPE: DNA
<213> ORGANISM: Artificial Sequence
<220> FEATURE:
<223> OTHER INFORMATION: Synthetic primer
```

<400> SEQUENCE: 18
tggaatcaag ggtcaggaag actgaaatgt tgtatgccga aggtcgtcag ctgaaagtga    60
rtctaagtct tttaatactt agaaaaattt tcatactttt caagactaag tgcactctac   120
t                                                                   121

<210> SEQ ID NO 19
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (113)..(113)
<223> OTHER INFORMATION: n is a, c, g, or t

<400> SEQUENCE: 19
cngggttggg gnaagggctg aatcttatag ttctttctgt gtgtcaagtt aacgcctcgt    60
rgagtcactt acgatctctt cgtttccatt tttcttcttg ttaaagaatg aanttgggtc   120
t                                                                   121

<210> SEQ ID NO 20
<211> LENGTH: 121
<212> TYPE: DNA
<213> ORGANISM: Artificial Sequence
<220> FEATURE:
<223> OTHER INFORMATION: Synthetic primer

<400> SEQUENCE: 20
aaaattgcct tagtacgaat taatactctt atatattctc aaaagacata tacccagacc    60
rtacttgtgg gattacaccg gctatgttgt ggttgttttg tgaagacata tttaagtact   120
c                                                                   121

<210> SEQ ID NO 21
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t

<400> SEQUENCE: 21
gttaagcttc tgtgaagcca aaagtntttt tttnncgaag tgtttagtta aaaaagttgc    60
rttgtttggc caagctttta ggaaaaagat aagtatttcg agtcgttgta gaaactgcac   120
t                                                                   121

<210> SEQ ID NO 22
<211> LENGTH: 121

```
<212> TYPE: DNA
<213> ORGANISM: Artificial Sequence
<220> FEATURE:
<223> OTHER INFORMATION: Synthetic primer

<400> SEQUENCE: 22
ctgttcaaga gcaattcagt catttgttct tcaggtaatc ttgtttattc ccaaattgtg    60
scaatcaatt tggttctcat cattggtatc agagacctaa tcatctgacc tgtgcgatgg   120
g                                                                  121

<210> SEQ ID NO 23
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 23
tacacnggta aaactgacaa ggcatcagcg ttagccaata atgaactttt agcgcggaac    60
ytcaagtgac caagtgcatg aaaccaaatc aagaaggtaa agatatgntg atcacctgaa   120
t                                                                  121

<210> SEQ ID NO 24
<211> LENGTH: 121
<212> TYPE: DNA
<213> ORGANISM: Artificial Sequence
<220> FEATURE:
<223> OTHER INFORMATION: Synthetic primer

<400> SEQUENCE: 24
tggatatagg aaagatcact tagaaattca acaatctttt tcgtctttaa gagcctgtag    60
rcttctttag catctacaca tcaaaattct ccagacattt caaattatat acagtccacg   120
a                                                                  121

<210> SEQ ID NO 25
<211> LENGTH: 121
<212> TYPE: DNA
<213> ORGANISM: Artificial Sequence
<220> FEATURE:
<223> OTHER INFORMATION: Synthetic primer

<400> SEQUENCE: 25 actctttat tcgtaatgtt catagacgaa agagacgatc cttcgctcct gtgagcagga    60
yggtgttcca atgtgcaagg ccctttcctg aagaggtcga aaattcacga cccattcata   120
g                                                                  121

<210> SEQ ID NO 26
<211> LENGTH: 113
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (93)..(93)
```

<223> OTHER INFORMATION: n is a, c, g, or t

<400> SEQUENCE: 26
taagtacaag tttaaggatt caagttatct cttaaattag ctttcagaac atgatgacat    60
kctttctgct tgcgatggg acagatggaa tantcaagtc atgttgactt gat    113

<210> SEQ ID NO 27
<211> LENGTH: 121
<212> TYPE: DNA
<213> ORGANISM: Artificial Sequence
<220> FEATURE:
<223> OTHER INFORMATION: Synthetic primer

<400> SEQUENCE: 27
aataatgaca ttcgatttgt cagcaactaa atcaaagcac tccatcaagc aacaataaga    60
katccggact ttcatccgca tgcaccctca cagcaagaaa gttccccata ctacttacac    120
t    121

<210> SEQ ID NO 28
<211> LENGTH: 119
<212> TYPE: DNA
<213> ORGANISM: Artificial Sequence
<220> FEATURE:
<223> OTHER INFORMATION: Synthetic primer

<400> SEQUENCE: 28 gttttccaa tgtatccacc aaatacagtc atgccttttg tatattggga tcaacctart    60
gtgttcgcgc cagttcatta tcgctcttct tatagatgta tcgcacctgg aagttgcat    119

<210> SEQ ID NO 29
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 29 cttttctct tattnccttt tnattttctt gttttgctac taaaagcttg aagttctatt    60
ktgcaatgtg catacttgct tgaagtctcg tattcacatg ttaagaccttt ctctttagaa    120 a    121

<210> SEQ ID NO 30
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (28)..(28)
<223> OTHER INFORMATION: n is a, c, g, or t

<400> SEQUENCE: 30
cttagatcaa aagtgaatac aacaaaangt taccggatga ttccatttct aagccgacca    60
yatccacagt aaaccatat gtagcaagat agaaattgaa aacaattatc accgtacaca    120
t                                                                          121

<210> SEQ ID NO 31
<211> LENGTH: 121
<212> TYPE: DNA
<213> ORGANISM: Artificial Sequence
<220> FEATURE:
<223> OTHER INFORMATION: Synthetic primer

<400> SEQUENCE: 31
gcgcccacga acattgccgt gttgggagtt accaagaggc tgatgcagaa tgtacaaagt      60
ygtctgcaat acgacacgta tggttttgga gacattgtct tatttggtaa cggggagaga    120
a                                                                          121

<210> SEQ ID NO 32
<211> LENGTH: 121
<212> TYPE: DNA
<213> ORGANISM: Artificial Sequence
<220> FEATURE:
<223> OTHER INFORMATION: Synthetic primer

<400> SEQUENCE: 32
ctcgtcttct ttcttgatct tttaagcacc gcgttgatga aattttcgt gttttgctta       60 yacgagttgc attttgaaa taatgttagt acgttttcag attatgatca tagacttcaa     120
a                                                                          121

<210> SEQ ID NO 33
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (108)..(108)
<223> OTHER INFORMATION: n is a, c, g, or t

<400> SEQUENCE: 33
aatagatcaa atcaacaatg gagtttaatt gagaaaaaga agaagccaat aacagatatc      60
rcacaaattt ggattagaat cgagnagaat gagnacatag atcacacnaa ttcctcagaa    120
t                                                                          121

<210> SEQ ID NO 34
<211> LENGTH: 121
<212> TYPE: DNA
<213> ORGANISM: Artificial Sequence
<220> FEATURE:
<223> OTHER INFORMATION: Synthetic primer

<400> SEQUENCE: 34
ggggcggagc tagagttgta gttacggatt tagcagaacg aatgacactt ctatagggct      60
yaagtagttg gaatgaatca gttactactg atcaaagtta tcaaaagttt tcgtattgtc    120
t                                                                          121

<210> SEQ ID NO 35
<211> LENGTH: 121
<212> TYPE: DNA
<213> ORGANISM: Artificial Sequence
<220> FEATURE:
<223> OTHER INFORMATION: Synthetic primer

<400> SEQUENCE: 35
cttaagaaca ctcccacttc ggcttaagca ccatcgaaaa gacaaactag aaccagctca      60
ygcatacaat aaaaagcata cacaaaagtt acgaaccata attggtcgta aaatggagca     120
g                                                                    121

<210> SEQ ID NO 36
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (83)..(83)
<223> OTHER INFORMATION: n is a, c, g, or t

<400> SEQUENCE: 36
tcttggaaaa tcgatatcag aaatggaaat cccatcgggc tgtcaggagt tgactcttag      60
ytatctttgt gaaagttcca aantggggtt tggagagaga gatgttttcg tggataaagg     120
t                                                                    121

<210> SEQ ID NO 37
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (75)..(75)
<223> OTHER INFORMATION: n is a, c, g, or t

<400> SEQUENCE: 37
cttaagaaca ctcccacttc ggcttaagca ccatcgaaaa gacaaactag aaccagctca      60
ygcatacaat aaaangcata cacaaaagtt acgaaccata attggtcgta aaatggagca     120
g                                                                    121

<210> SEQ ID NO 38
<211> LENGTH: 121
<212> TYPE: DNA
<213> ORGANISM: Artificial Sequence
<220> FEATURE:
<223> OTHER INFORMATION: Synthetic primer

<400> SEQUENCE: 38
ctttatcgat gattatctgc tctggaggtg tacgtttctc aacagtttct atacttgcaa      60
yagttaggct tgatgttgtt aaagcctaac tactcgcaaa cacactcaga accaaatgca     120
a                                                                    121

<210> SEQ ID NO 39
<211> LENGTH: 121
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (110)..(110)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t

<400> SEQUENCE: 39
atcggcatcc tcaagactat ccattgttat aaaagcaaaa ccacgagaga tacgagaacg    60
yggctccaca accaagaaag ctgatttnac ctggtcgaca gaaagtaaan gaaaaanctc   120
a                                                                  121

<210> SEQ ID NO 40
<211> LENGTH: 121
<212> TYPE: DNA
<213> ORGANISM: Artificial Sequence
<220> FEATURE:
<223> OTHER INFORMATION: Synthetic primer

<400> SEQUENCE: 40
cagatatttt cagtaaaatc gtaattagat ccttgagatc taactgcact ctaatgtcac    60
ytcaggaggc aaaaccaaag aagattttt cttccagctc cattaactaa accgcatact   120
c                                                                  121

<210> SEQ ID NO 41
<211> LENGTH: 292
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (138)..(139)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t

<400> SEQUENCE: 41
caaccatccc tcaactaacg tgggacactt aacaatctac cgcacaccca ggcccgccta    60
ctagagcgtg gacgaaataa tgagggccct acatggagac gcacngtaag agggatgagt   120
ctggctctga ccatgtgnnt aantcaatcc taaaagctat ctcatgaagt gaggattgac   180
cacnaccata caacragcta caaacaagcc atccctcaac caatatggga cattaaacac   240
ttcttaagtt ccaacttana agtgttgtct tgaaggattg agcaagtgtc aa           292

<210> SEQ ID NO 42

```
<211> LENGTH: 218
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (22)..(22)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t

<400> SEQUENCE: 42
atgcatgagg gcaatacaag cnttgaatcg aaatgactgt ttaatctcgt ggactgtata      60
taatttgaaa tgtctggaga attttgatgt gtagatgcta aagaagncta caggctcyta    120
aagacgaaaa agattgttga atttctaagt gatctttcct atatccaccc ctaagctgcc    180
agcgctgggg gttcctttct cttggttggc cttcctag                            218

<210> SEQ ID NO 43
<211> LENGTH: 252
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (157)..(157)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t

<400> SEQUENCE: 43
ccgttttaac atatgtacat ggcttgtctt agttactaat atcatctgat accatgtgca     60
aacatgactt gggaatgtgg gacttaatat acttgtaacc mtgtgttttg ttattgaaat   120
taaagttcag tgttatgttt gtttaaaacg gccactnggt acatgttata cngctcttgg   180
tctaagctct tatctacata ctataaataa cttttttgt tcttggtttc tatcaccaat     240
tattatttta tc                                                         252

<210> SEQ ID NO 44
<211> LENGTH: 184
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t

<400> SEQUENCE: 44
atttctggat ttctacttgt aaaagggaag cccggtgcac taaagcgccc gttatgcaag     60
ggggccgggg aaggttcagc ctgcaacggt ccattgtacg yagccttanc ctgcattct    120 ncaagaggct gtttccacag cttgaatccg tgacctcctg gtcacatggc aacaactta    180 ccca                                                                 184
```

METHODS AND COMPOSITIONS FOR PRODUCING CAPSICUM PLANTS WITH POWDERY MILDEW RESISTANCE

CROSS REFERENCE TO RELATED APPLICATIONS

This application is a divisional of U.S. application Ser. No. 13/598,496, filed Aug. 29, 2012, which claims benefit of U.S. Provisional Application Ser. No. 61/529,205, filed Aug. 30, 2011, each of which is incorporated herein by reference in entirety.

INCORPORATION OF SEQUENCE LISTING

The sequence listing that is contained in the file named "SEMB004US_ST25.txt" which is 18,583 bytes (measured in MS-WINDOWS), created Aug. 29, 2012, is filed herewith by electronic submission and is incorporated herein by reference.

BACKGROUND OF THE INVENTION

Field of the Invention

The invention provides pepper plants having Powdery mildew fungal resistance and methods for obtaining such pepper plants.

Description of Related Art

Peppers are one of the most popular fruit-bearing plants grown worldwide. Pepper plants are grown in a wide range of climates, in open fields as well as in greenhouses. Peppers belong to the genus *Capsicum*, of the nightshade family, Solanaceae (e.g. *Capsicum annuum*). The term "pepper" may refer to the plant as well as its fruit. Peppers are commonly broken down into three groupings: bell peppers, sweet peppers, and hot peppers. Most popular pepper varieties fall into one of these categories, or as a cross between them. However, these groupings are not absolute, as both "hot pepper" and "sweet pepper" encompass members belonging to several different species. Additionally, members of each of the groups may be different cultivars of the same species. For example, the bell pepper, the jalapeño pepper, and the "Thai sweet" all belong to the species *Capsicum annuum* L. Hot peppers, including some inedible varieties, are grown for edible as well as ornamental and medicinal uses. While there are pungent (i.e. "hot") varieties of *C. annuum*, many well known hot peppers are members of different species. For example, both the cayenne pepper and the Tabasco pepper are varieties of *Capsicum frutescens*, while the hottest peppers, including the habanero and naga varieties, are members of *Capsicum chinense*.

Pepper breeding efforts have focused in part on growing pepper plants resistant to diseases such as Powdery Mildew (PM), caused by the fungus *Leveillula taurica*. Powdery mildew caused by the fungus *Leveillula taurica* exhibits a worldwide disease distribution and may affect peppers grown under greenhouse or field conditions.

Symptoms of pepper Powdery Mildew caused by the fungus *Leveillula taurica* during the initial stages of infection may include visible light-green to bright-yellow blotches appearing on upper and lower surfaces of leaves followed by a powdery, white growth caused by the sporulation of the fungus. Under some environmental conditions these areas may later turn necrotic. Infected leaves may also curl upward and exhibit a visible powdery, white growth on the underside of leaves. When lesions are numerous, they often coalesce, resulting in general chlorosis and leaf drop. The disease generally progresses from older to younger leaves. Common commercial fruit production yield losses come from fruits on affected plants being overexposed to sunlight and developing sunscald as well as reduced yield due to leaf loss.

Airborne conidia (asexual fungal spores) from previously infected crops or weeds can be carried long distances by wind and act as initial sources of inoculum. The wide host range of these fungi exacerbate disease spread and reduce the ability of agronomic practice to control disease incidence. Disease control is commonly managed by application of fungicides before infection or immediately after the first symptoms are observed. In addition to the cost of pesticide application, there is increasing social pressure to reduce the pesticide load in the environment.

There is a need for pepper varieties having resistance to Powdery Mildew (PM), caused by the fungus *Leveillula taurica*.

BRIEF SUMMARY OF THE INVENTION

In one aspect, the present invention provides a method of identifying a pepper plant of the genus *Capsicum* that displays improved resistance to Powdery Mildew, the method comprising: detecting in a first pepper plant at least one allele of a marker that is associated with the resistance or improved resistance, wherein the marker is genetically linked within 10 centiMorgans (cM) of markers NE0235653, NE0237841, NE0237985, NE0239990, or NE0240958, on pepper chromosome 4. In one embodiment, there is provided such a method, further wherein the marker is localized within a chromosomal interval defined by and including the termini NE0235653 and NE0240958 on pepper chromosome 4. In another embodiment, the marker is localized within a chromosomal interval defined by and including the termini NE0236790 and NE0237985 on pepper chromosome 4. In yet another embodiment, the marker is localized within a chromosomal interval defined by and including the termini NCANN005704058 and NCANN005704049.

In a particular embodiment the Powdery Mildew causal agent is *Leveillula taurica*. Provided in another embodiment is such a method wherein the resistance or improved resistance is assayed by exposing the plant to Powdery Mildew and identifying plants with reduced sporulation of *L. taurica*, relative to control plants.

In certain embodiment of the method, the detecting comprises detecting at least one allelic form of a single nucleotide polymorphism by PCR, single strand conformational polymorphism analysis, denaturing gradient gel electrophoresis, cleavage fragment length polymorphism analysis, TAQMAN assay, and/or DNA sequencing.

In another embodiment of the method, at least one allele of a marker associated with resistance to Powdery Mildew is in pepper line PBC167, or a progeny plant thereof. Yet another embodiment comprises phenotypically assaying said first pepper plant or a plant isogenic thereto for resistance to Powdery Mildew infection. Still another embodiment of the method comprises selecting the first pepper plant from a population of pepper plants based on the presence of said allele of a marker that is associated with the resistance or improved resistance to Powdery Mildew infection. In a particular embodiment, the method further comprises crossing the selected first pepper plant or germplasm with a second pepper plant to obtain a progeny plant of a subsequent generation. The method may further comprise backcrossing the progeny plant of a subsequent generation and at least one further subsequent generation thereof to a recurrent parent until a backcrossed progeny plant is produced that comprises said improved resistance to Powdery Mildew.

In certain embodiments of the method, the marker is selected from the group consisting of NE0235653, NE0238847, NE0237736, NE0236986, NE0236080, NE0237755, NE0239177, NE0238603, NE0238046, NE0237823, NE0230886, NE0240044, NE0237442, NE0238362, NE0238536, NE0236808, NE0238448, NE0241383, NE0240496, NE0237841, NE0239164, NE0240741, NE0236790, NE0238624, NE0240275, NE0238899, NE0238734, NE0240256, NE0237985, NE0239638, NE0239147, NE0240589, NE0237975, NE0239291, NE0235654, NE0238449, NE0240786, NE0239990, NE0231151, NE0240438, NE0237121, NE0238426, NE0235272, NE0237901, NE0237351, NE0241057, NE0237348, and NE0240958.

In some embodiments of the method, the marker is selected from the group consisting of NCANN005704058, NCANN005704056, NCANN005704052, and NCANN005704049.

In other embodiments the marker is one or more markers selected from the group consisting of NE0237823, NE0237442, NE0236808, NE0238624, NE0236790, NE0237985, NE0239147, NE0240438, and NE0237348. In particular embodiments the marker is NE0236790 or NE0237985. Further, the marker may map within 35 cM, 20 cM, 10 cM or 1 cM of a QTL which confers resistance to Powdery Mildew.

Another aspect of the invention relates to an agronomically elite pepper plant produced by the method described above, or an agronomically elite progeny plant thereof, that comprises said marker and chromosomal interval conferring resistance to Powdery Mildew. In one embodiment the chromosomal region conferring resistance to Powdery Mildew comprises a marker allele present in PBC167. Thus a particular embodiment of the invention provides a pepper plant wherein the chromosomal region is introgressed from PBC167.

In certain embodiments the pepper plant is further defined as comprising an allele from PBC167 at one or more of markers NE0235653, NE0238847, NE0237736, NE0236986, NE0236080, NE0237755, NE0239177, NE0238603, NE0238046, NE0237823, NE0230886, NE0240044, NE0237442, NE0238362, NE0238536, NE0236808, NE0238448, NE0241383, NE0240496, NE0237841, NE0239164, NE0240741, NE0236790, NE0238624, NE0240275, NE0238899, NE0238734, NE0240256, NE0237985, NE0239638, NE0239147, NE0240589, NE0237975, NE0239291, NE0235654, NE0238449, NE0240786, NE0239990, NE0231151, NE0240438, NE0237121, NE0238426, NE0235272, NE0237901, NE0237351, NE0241057, NE0237348, and NE0240958.

In other embodiments the pepper plant is further defined as comprising an allele from PBC167 at one or more of markers NCANN005704058, NCANN005704056, NCANN005704052, and NCANN005704049.

In some embodiments the invention provides a part of the pepper plant or progeny plant, including a seed capable of producing such a plant, and fruit.

In another aspect, the invention provides a pepper plant comprising at least a first introgressed chromosomal interval conferring resistance to Powdery Mildew, wherein the interval is a Powdery Mildew resistance contributing QTL on pepper chromosome 4 between markers NE0235653 and NE0240958. In one embodiment the interval is a Powdery Mildew resistance contributing QTL on pepper chromosome 4 between markers NE0237823 and NE0240438. In another embodiment the interval is a Powdery Mildew resistance contributing QTL on pepper chromosome 4 between markers NE0236808 and NE0239147. In yet another embodiment the interval is a Powdery Mildew resistance contributing QTL on pepper chromosome 4 between markers NE0236790 and NE0237985. In one embodiment the interval is a Powdery Mildew resistance contributing QTL on pepper chromosome 4 between markers NCANN005704058 and NCANN005704049.

In certain embodiments the pepper plant is defined as an agronomically elite plant displaying a trait selected from the group consisting of: enhanced plant vigor, altered leaf shape, altered plant height, determinacy, altered time to maturity, increased fruit size, blocky fruit shape, tapered fruit shape, altered fruit color, altered fruit weight, increased fruit pungency, reduced fruit pungency, enhanced fruit taste, enhanced surface appearance; altered seed number, altered seed size, altered locule number; altered pericarp thickness and toughness, improved shelf life enhanced fruit yield, adaptation to field growth, adaptation to greenhouse growth, and resistance to one or more diseases or disease causing organisms, relative to a control pepper plant. In some embodiments the pepper plant is homozygous for said chromosomal interval.

Another aspect of the invention relates to a method of producing a pepper plant of the genus *Capsicum* that displays improved resistance to Powdery Mildew, the method comprising: introgressing at least a first chromosomal interval that confers the improved resistance to Powdery Mildew, wherein the chromosomal interval maps to a position between the sequence represented by marker NE0235653 and marker NE0240958, or the chromosomal interval maps to a position between the sequence represented by marker NE0235653 and marker NE0237348, which each map to approximately 7.13 cM and 45.27 cM, respectively, on the genetic map of the linkage group termed pepper chromosome 4. In one embodiment the method the introgressing comprises: a) assaying pepper plants for the presence of at least one allele of a marker genetically linked to a chromosomal interval that confers resistance to Powdery Mildew; and b) selecting at least a first pepper plant comprising the allele and the chromosomal interval that confers resistance to Powdery Mildew, wherein the chromosomal interval maps to a position between the sequence represented by marker NE0235653 and marker NE0240958, or the chromosomal interval maps to a position between the sequence represented by marker NE0235653 and marker NE0237348, which map to approximately 7.13 cM and 45.27 cM, respectively, on the genetic map of the linkage group termed pepper chromosome 4; and c) self-pollinating the first pepper plant or cross pollinating the first pepper plant with a second pepper plant to produce at least a first progeny pepper plant comprising the chromosomal interval.

In certain embodiments of the method, selecting the first pepper plant further comprises selecting the plant based on the presence of a plurality of marker alleles that map to a position between the sequences represented by markers NE0235653 and NE0240958, or the chromosomal interval maps to a position between the sequence represented by marker NE0235653 and marker NE0237348, which map to approximately 7.13 cM and 45.27 cM, respectively, on the genetic map of the linkage group termed pepper chromosome 4. The method may also further comprise the step of d) selecting a progeny plant comprising the allele which is linked with resistance to Powdery Mildew and self-pollinating, backcrossing with a recurrent parent or cross-pollinating the progeny plant with a third pepper plant to produce 5 additional progeny plants. The method may also further comprise repeating step (d) about 2-10 times.

In another embodiment of the method, the alleles are from markers selected from the group consisting of NE0238847, NE0237736, NE0236986, NE0236080, NE0237755, NE0239177, NE0238603, NE0238046, NE0237823, NE0230886, NE0240044, NE0237442, NE0238362, NE0238536, NE0236808, NE0238448, NE0241383, NE0240496, NE0237841, NE0239164, NE0240741, NE0236790, NE0238624, NE0240275, NE0238899, NE0238734, NE0240256, NE0237985, NE0239638, NE0239147, NE0240589, NE0237975, NE0239291, NE0235654, NE0238449, NE0240786, NE0239990, NE0231151, NE0240438, NE0237121, NE0238426, NE0235272, NE0237901, NE0237351, and NE0241057.

In certain embodiments of the method, the marker is one or more markers selected from the group consisting of NE0237823, NE0237442, NE0236808, NE0238624, NE0236790, NE0237985, NE0239147, NE0240438, and NE0237348. In particular embodiments the marker is NE0236790 or NE0237985.

In one embodiment, the marker is one or more markers selected from the group consisting of NCANN005704058, NCANN005704056, NCANN005704052, and NCANN005704049.

The method may also comprise assaying the pepper plants by PCR, single strand conformational polymorphism analysis, denaturing gradient gel electrophoresis, cleavage fragment length polymorphism analysis, TAQMAN assay, and/or DNA sequencing.

In some embodiments the chromosomal interval that confers resistance to Powdery Mildew confers a reduction of *Leveillula taurica* sporulation of at least, or greater than, 25%, relative to a nonresistant control pepper line.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding" with reference to a nucleic acid are used to make the invention readily understandable by the skilled artisan however these terms may be used interchangeably with "comprise" or "comprising" respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

BRIEF DESCRIPTION OF THE SEQUENCES

TABLE 1

Figure 1:
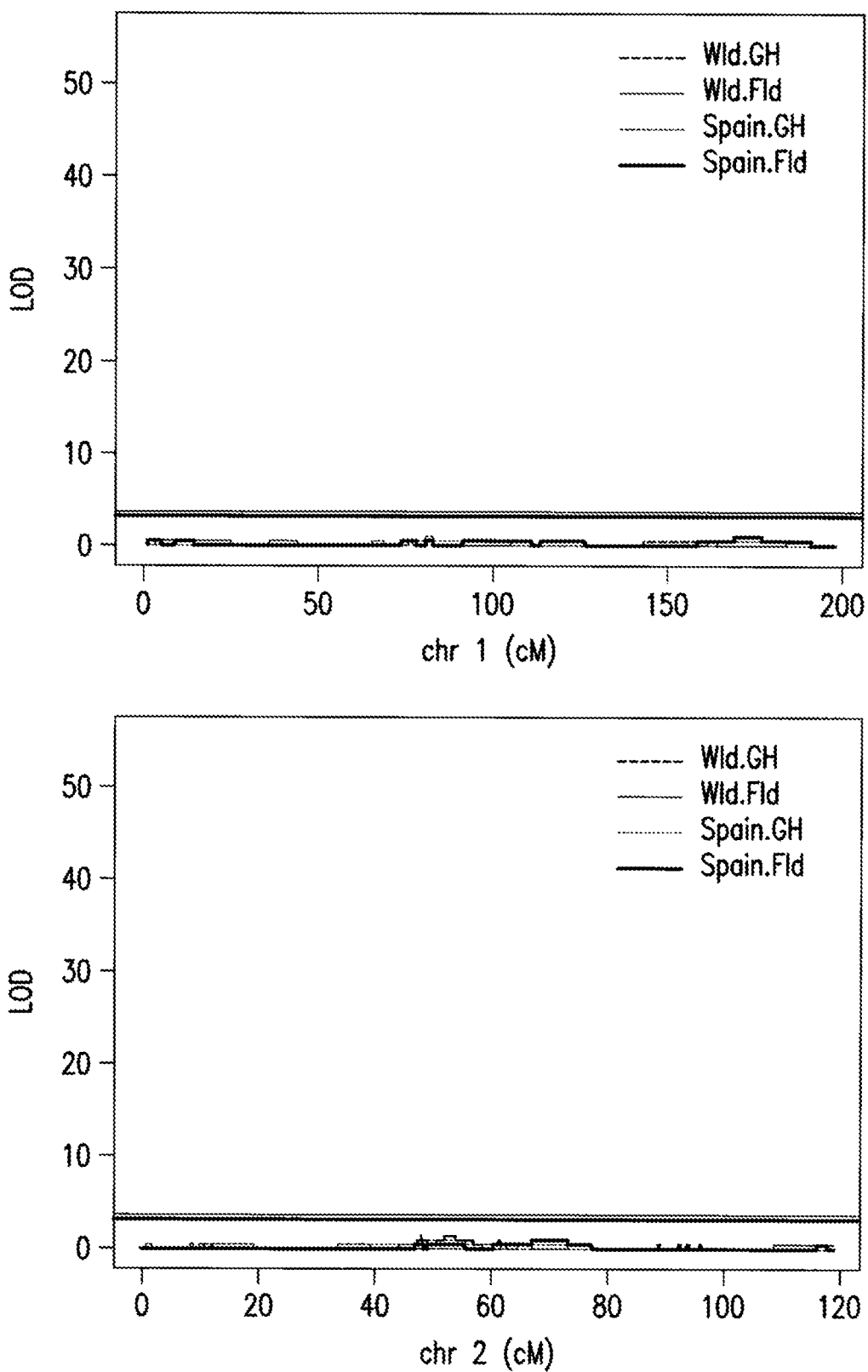
FIG. 1: Marker Regression Results. A QTL (Quantitative trait locus or loci) is detected on Chromosome 4 with the following methodology: R/qtl function scanone (method=mr) was used to scan for single QTL across the whole genome. Genome wide 1000 permutations were generated, 5% false discovery rate was utilized as significant threshold.
Figure 1:
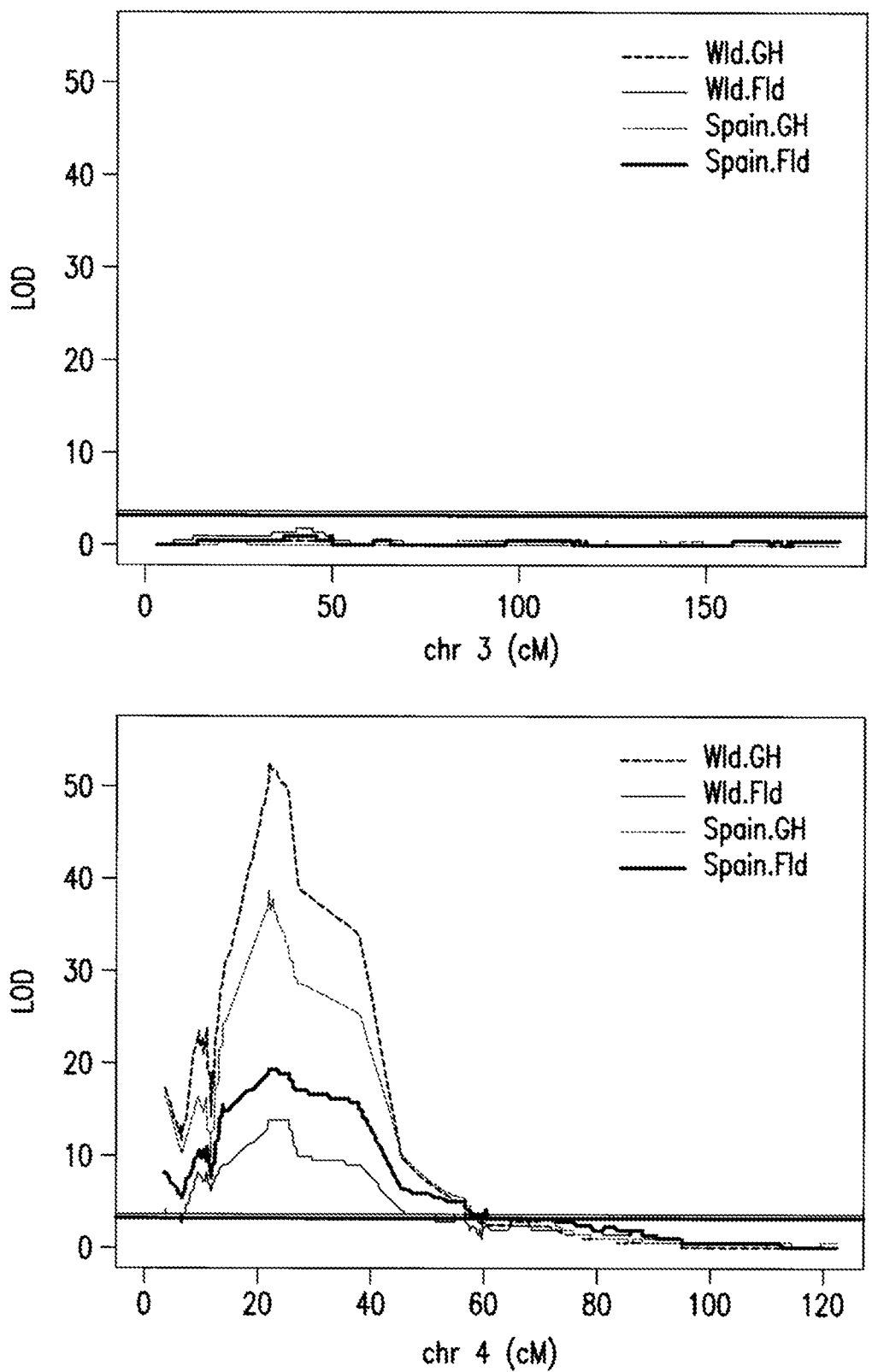
Figure 1:
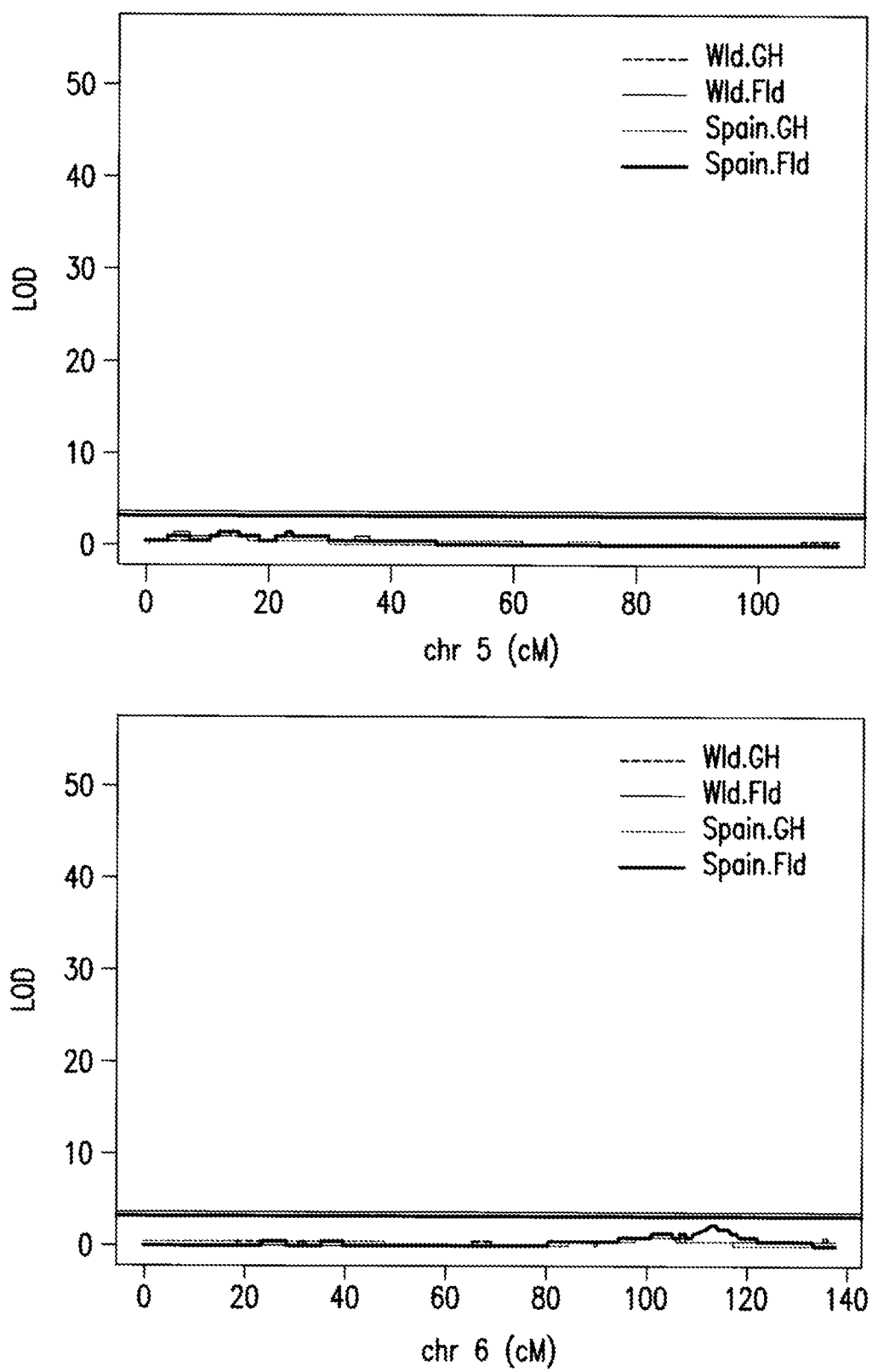
Figure 1:
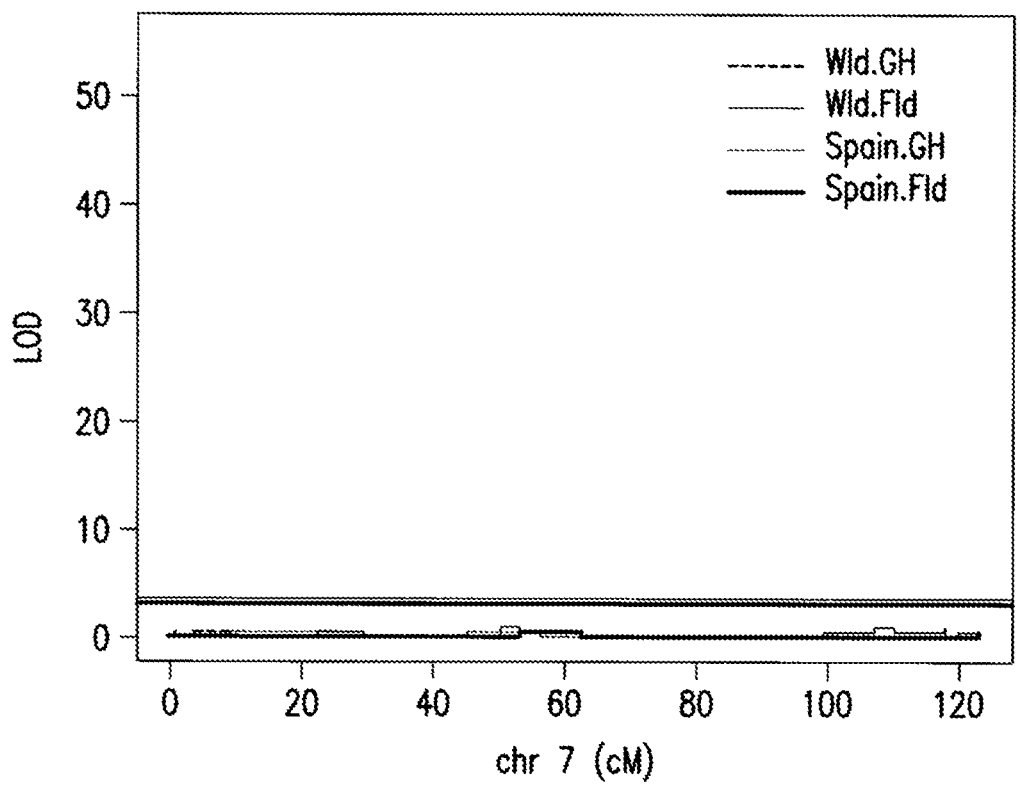
Figure 1:
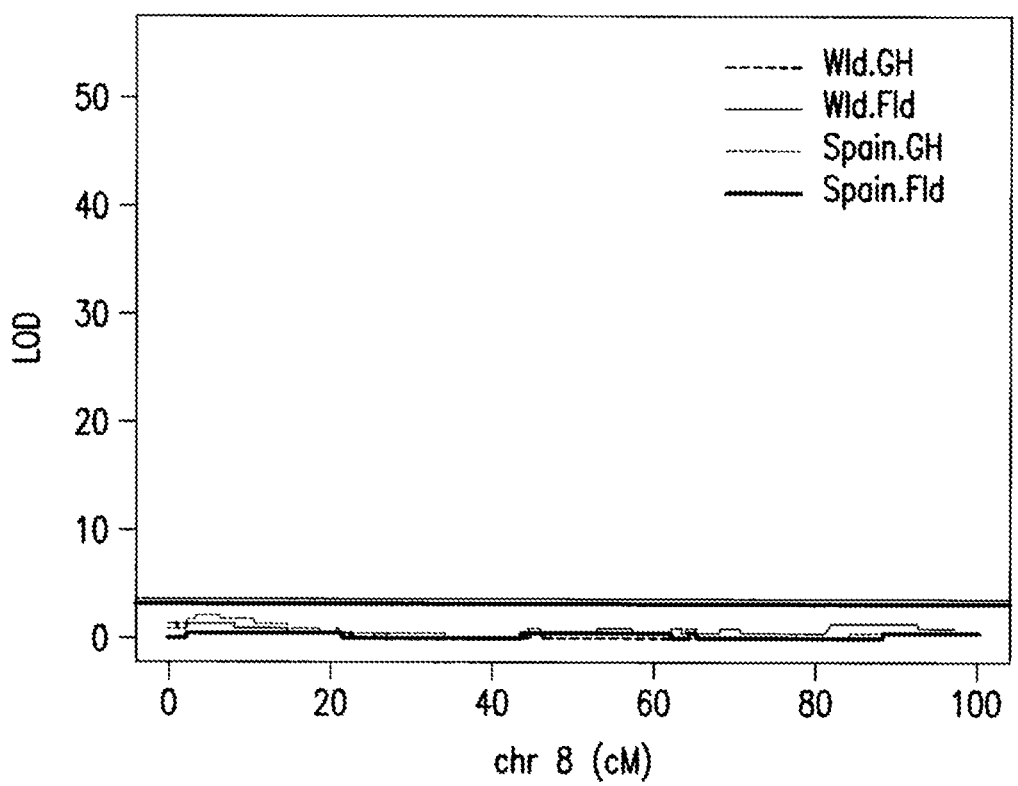
Figure 1:
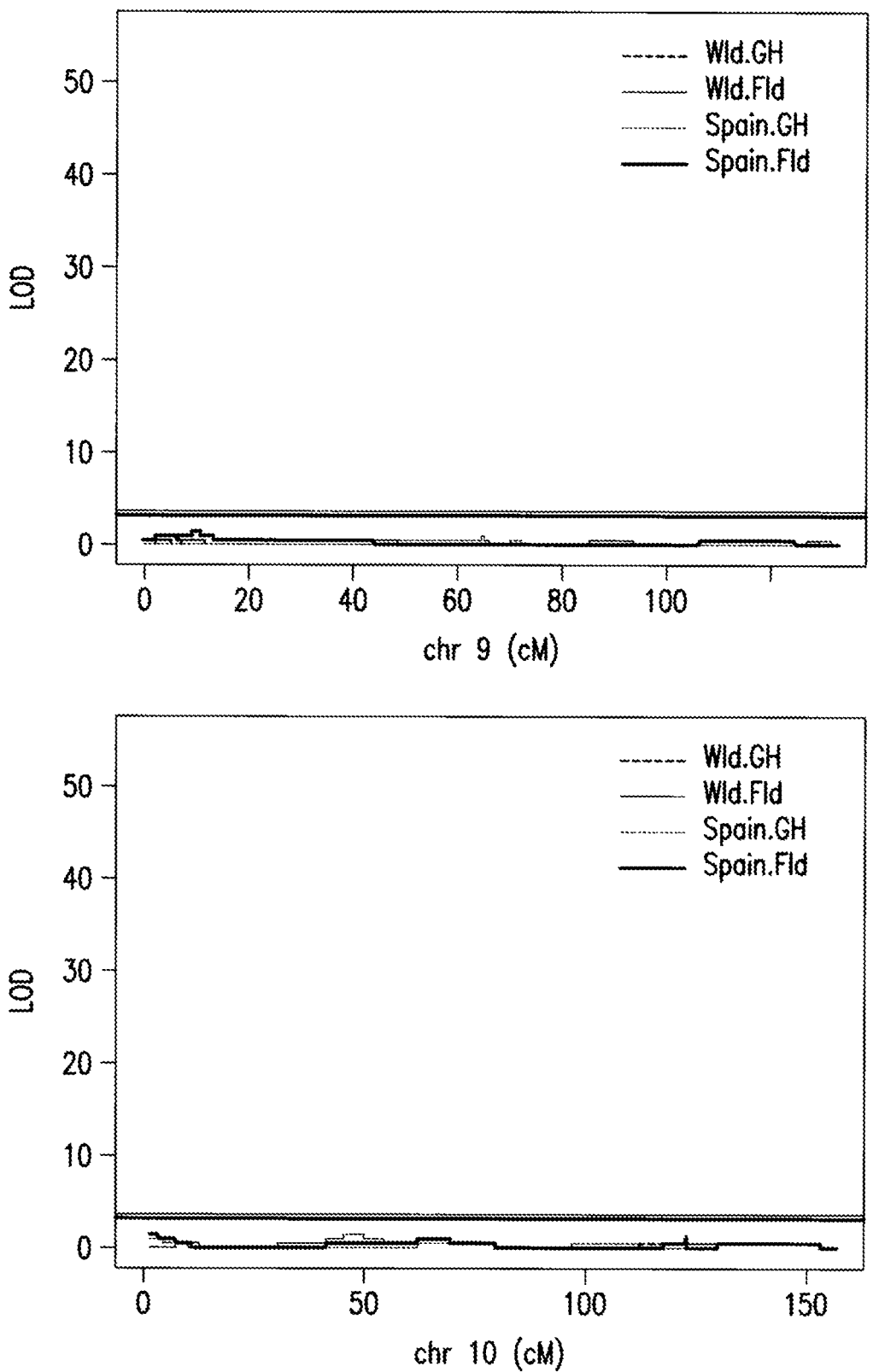
Figure 1:
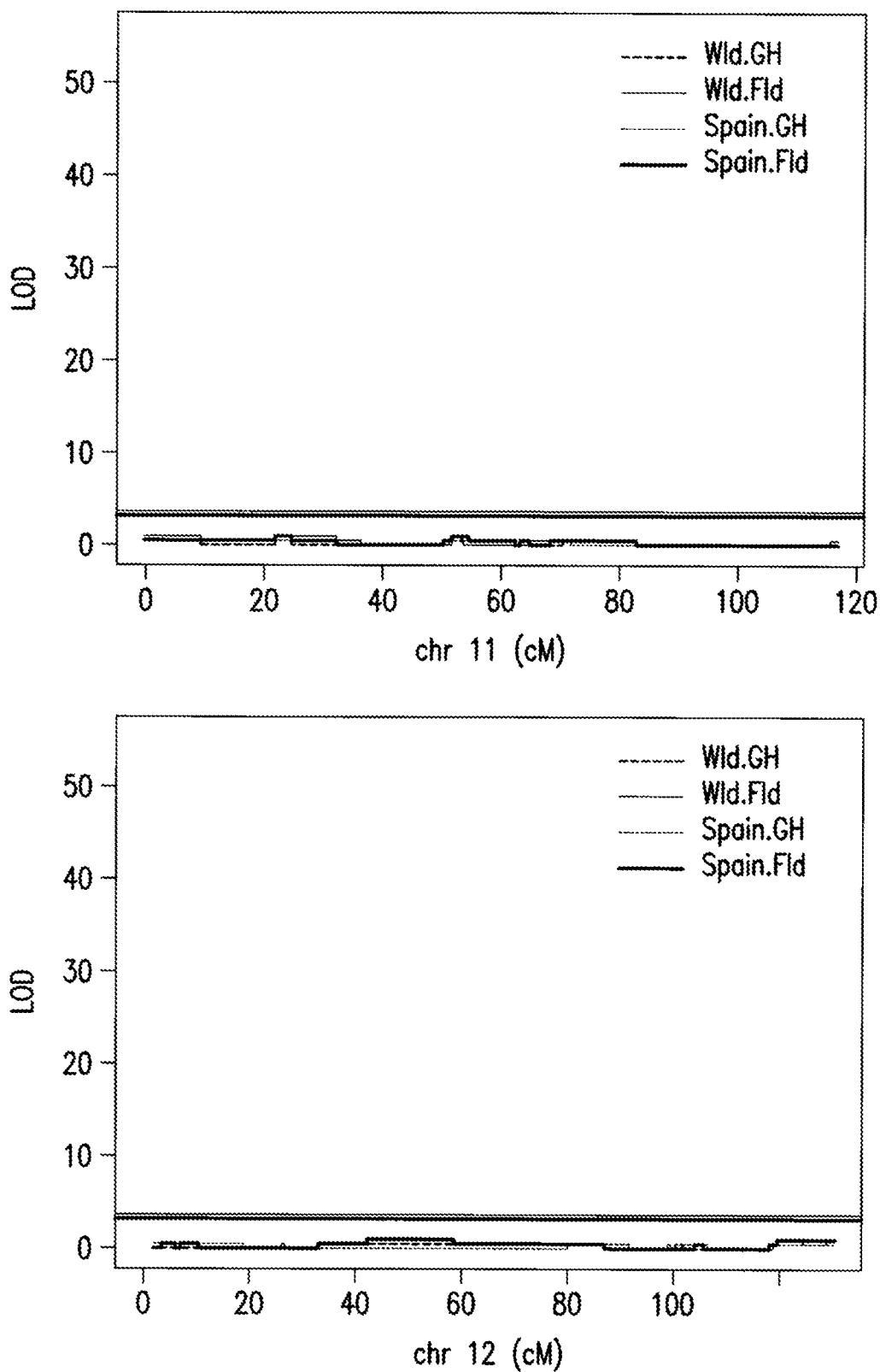
Figure 2:
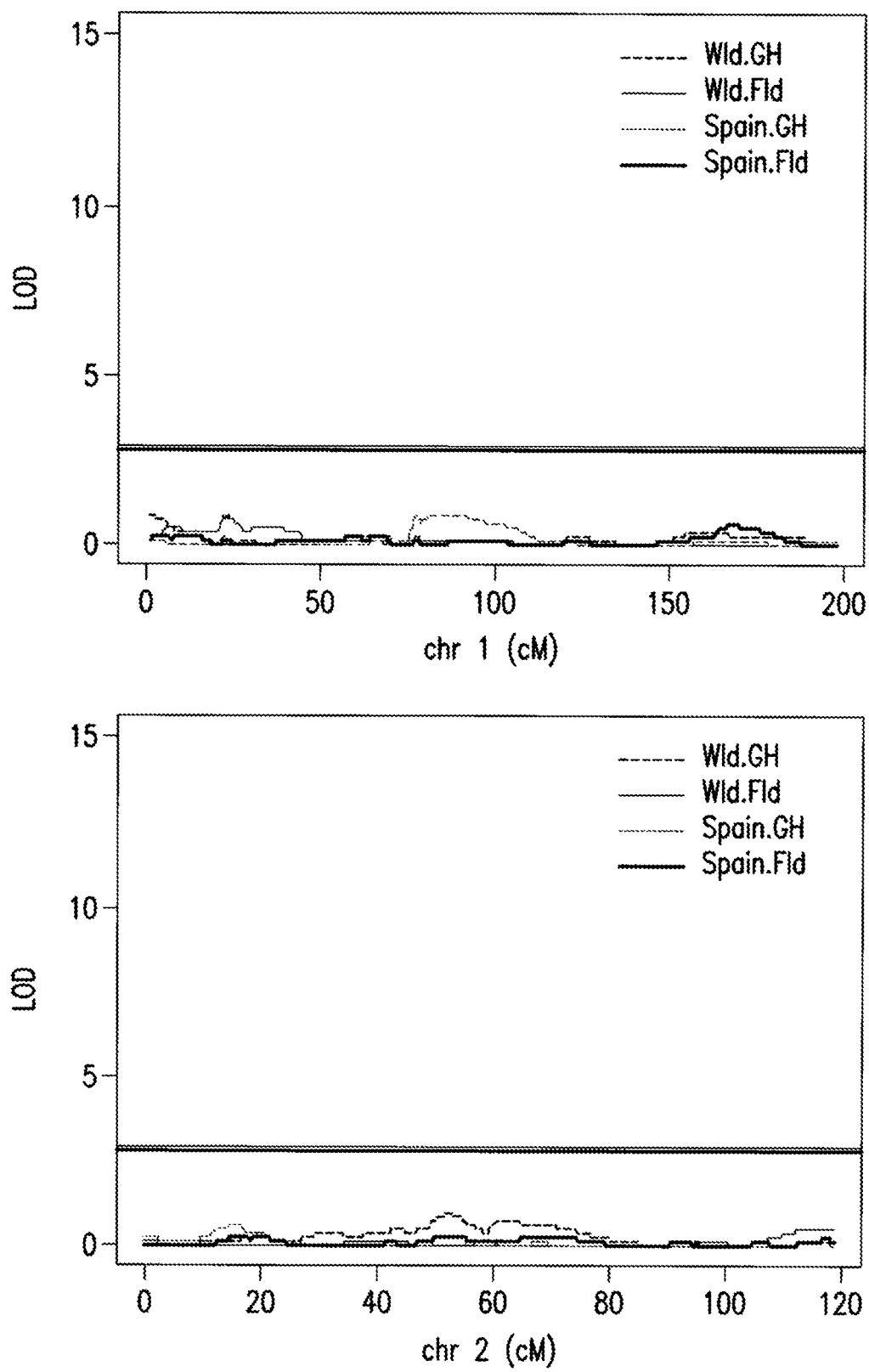
FIG. 2: Interval Mapping Results. A QTL on chromosome 4 was identified by all four sets of phenotypic data at almost the same location by interval mapping using a non-parametric model for adjusted phenotypic data at 1 cM intervals. LOD score significance was based on the 5% alpha threshold obtained with 1,000 permutations genome-wide.
Figure 2:
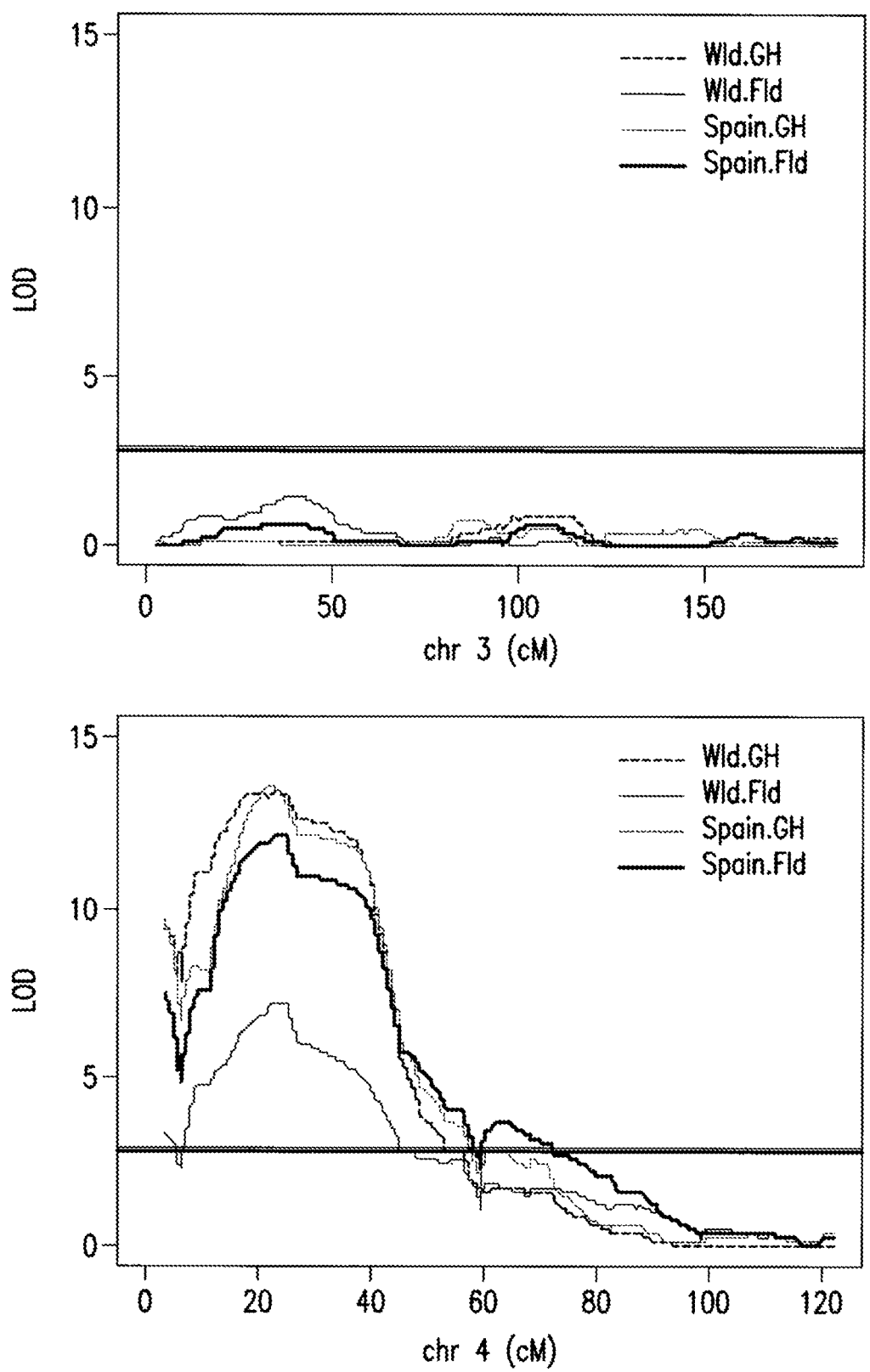
Figure 2:
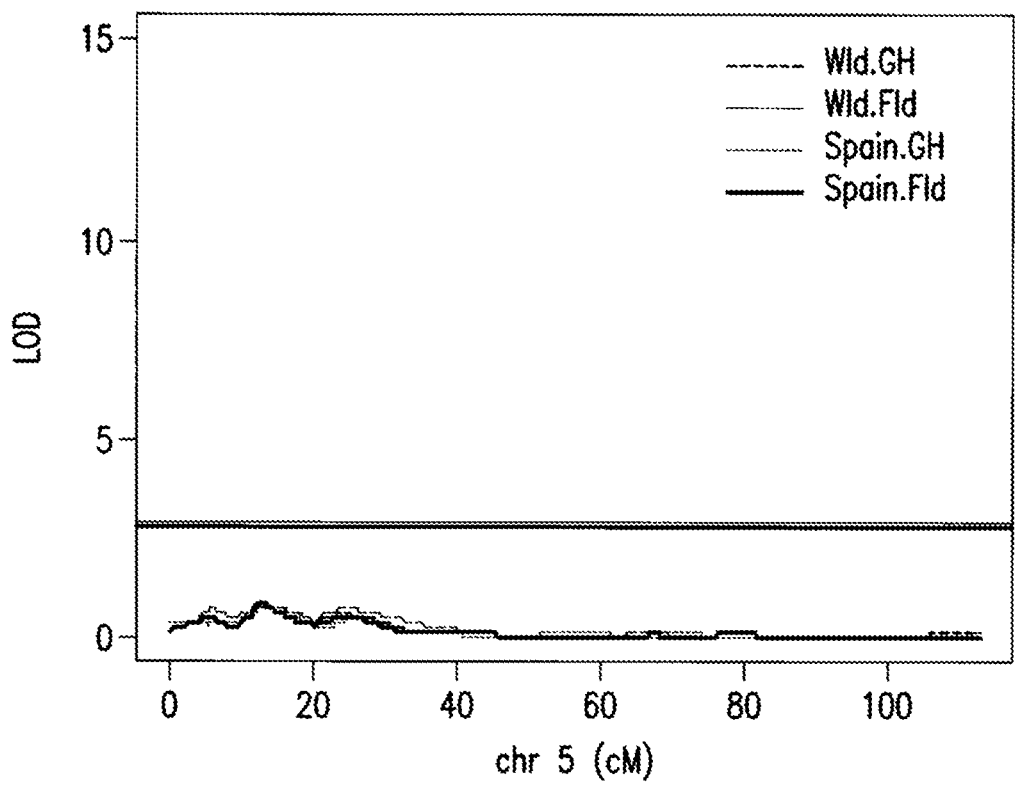
Figure 2:
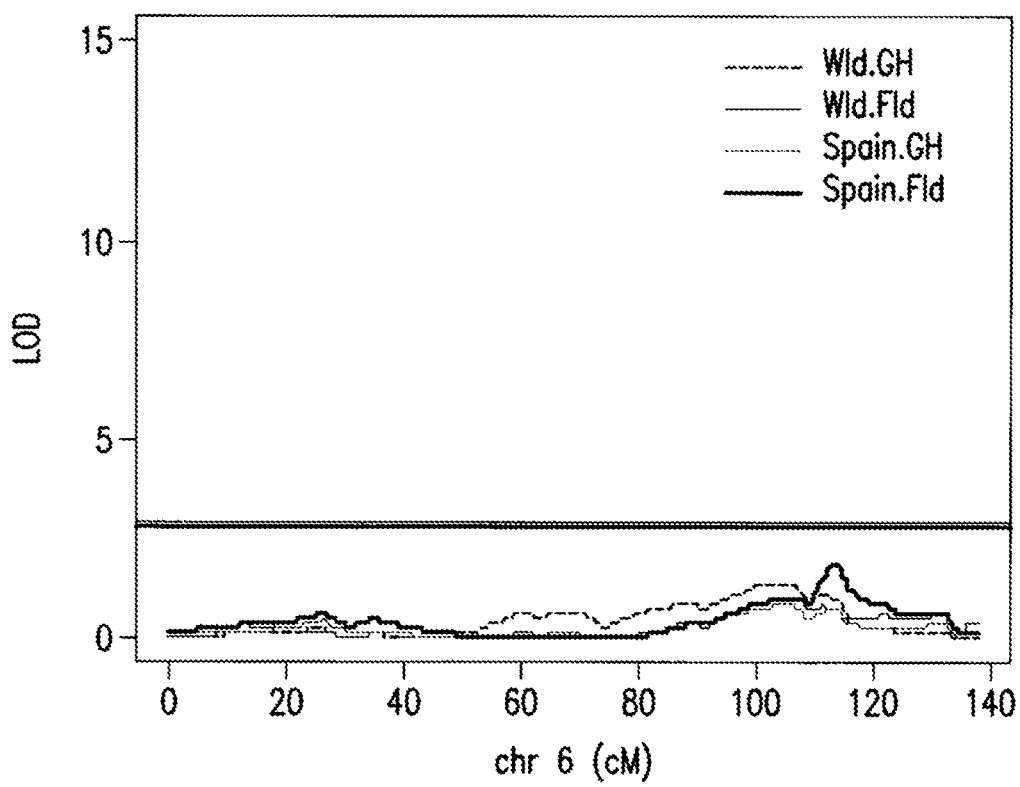
Figure 2:
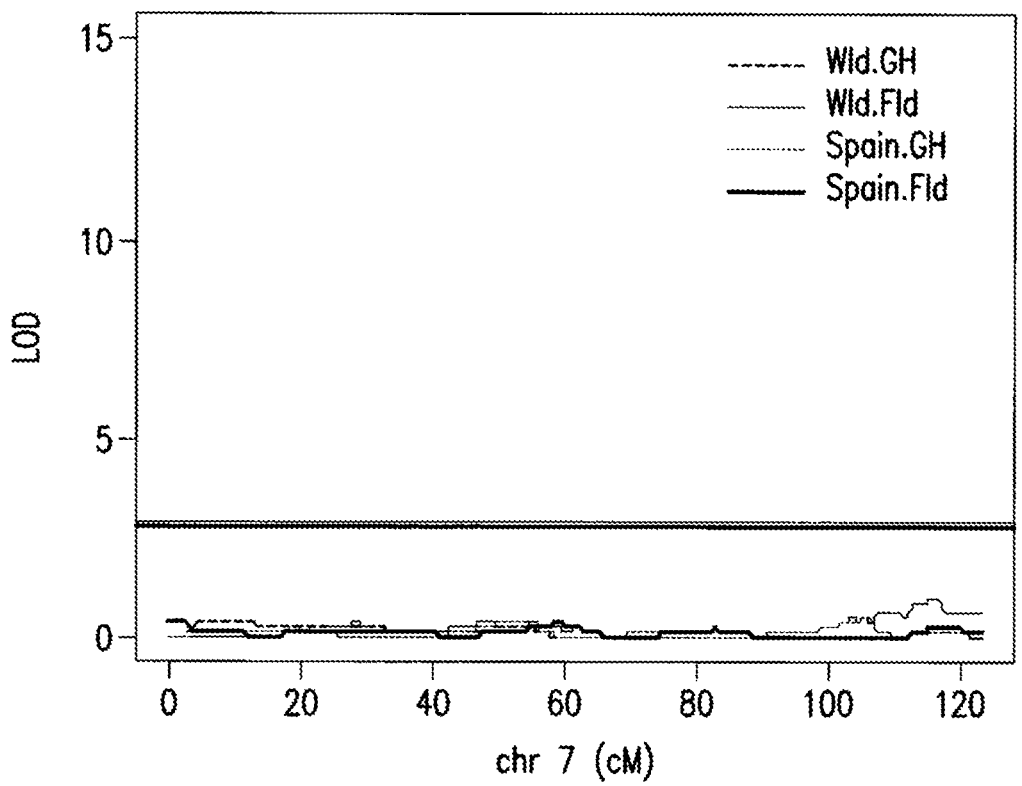
Figure 2:
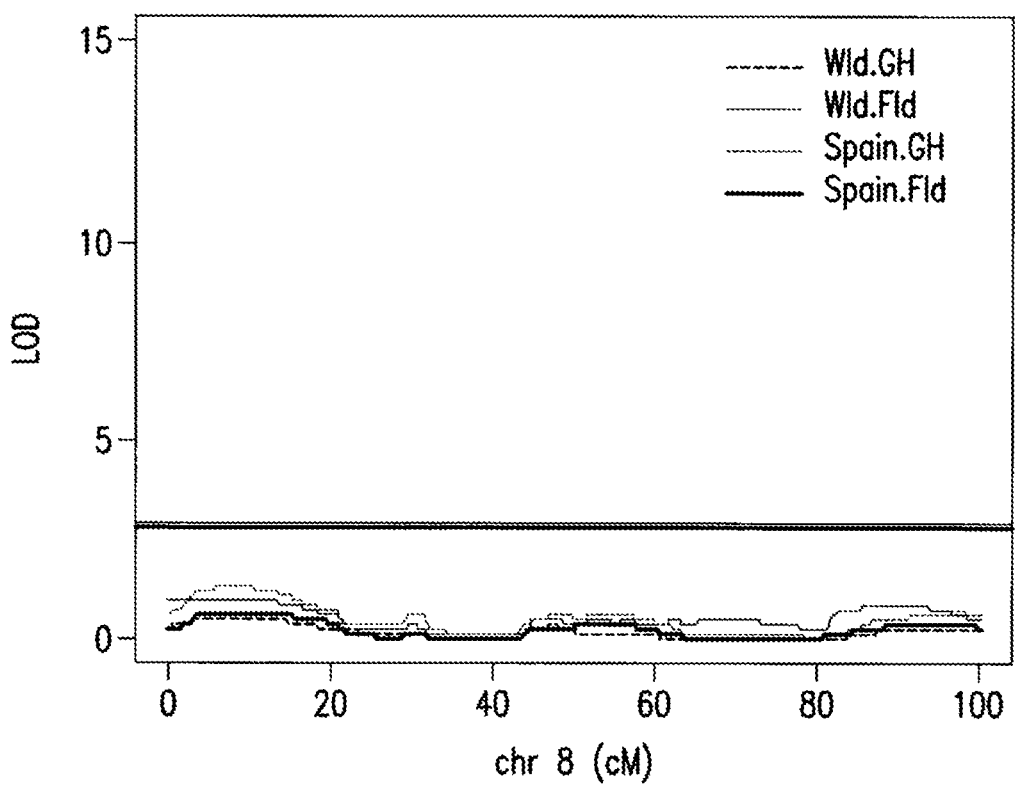
Figure 2:
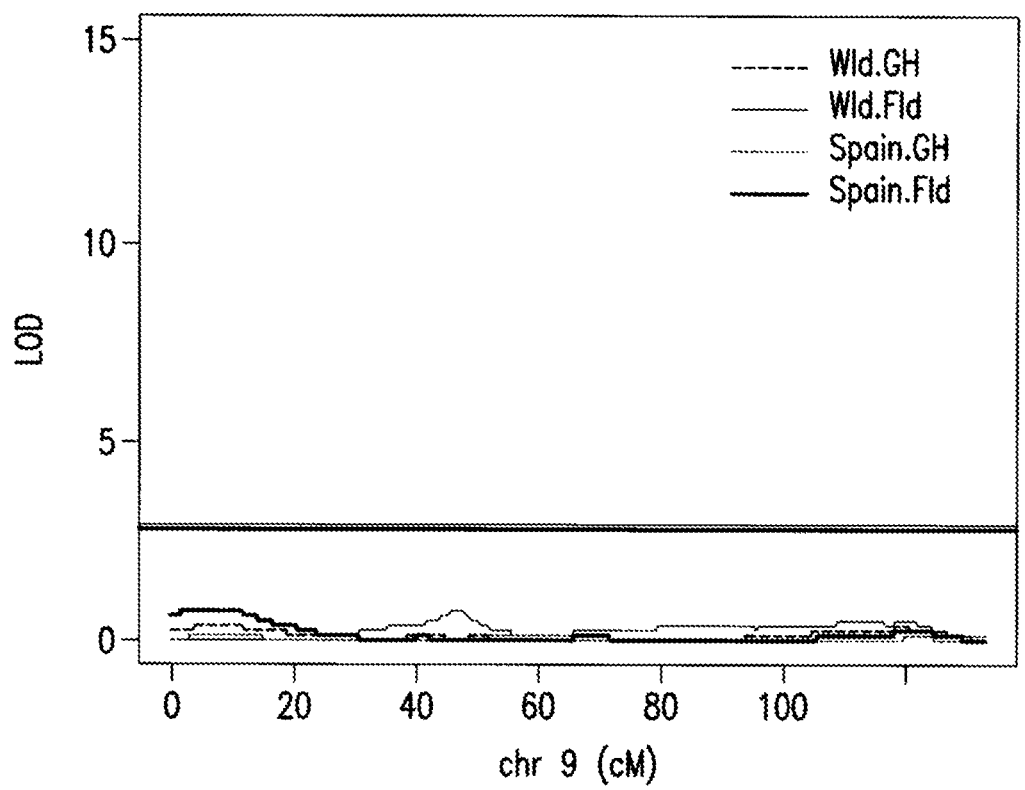
Figure 2:
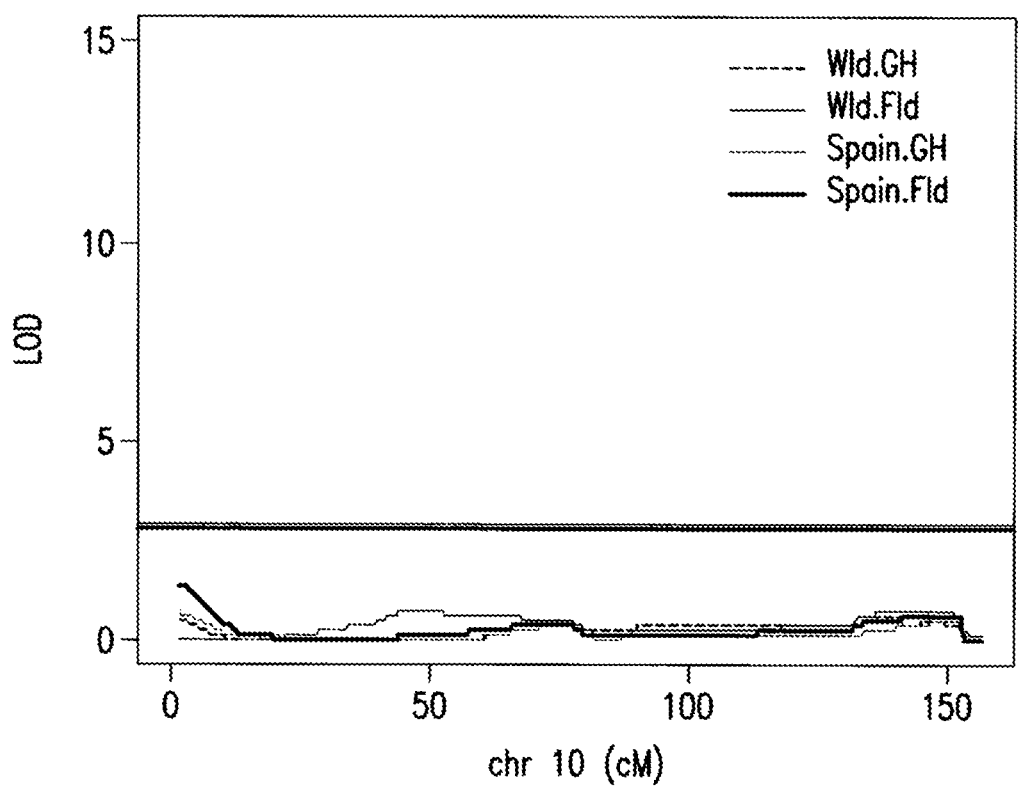
Figure 2:
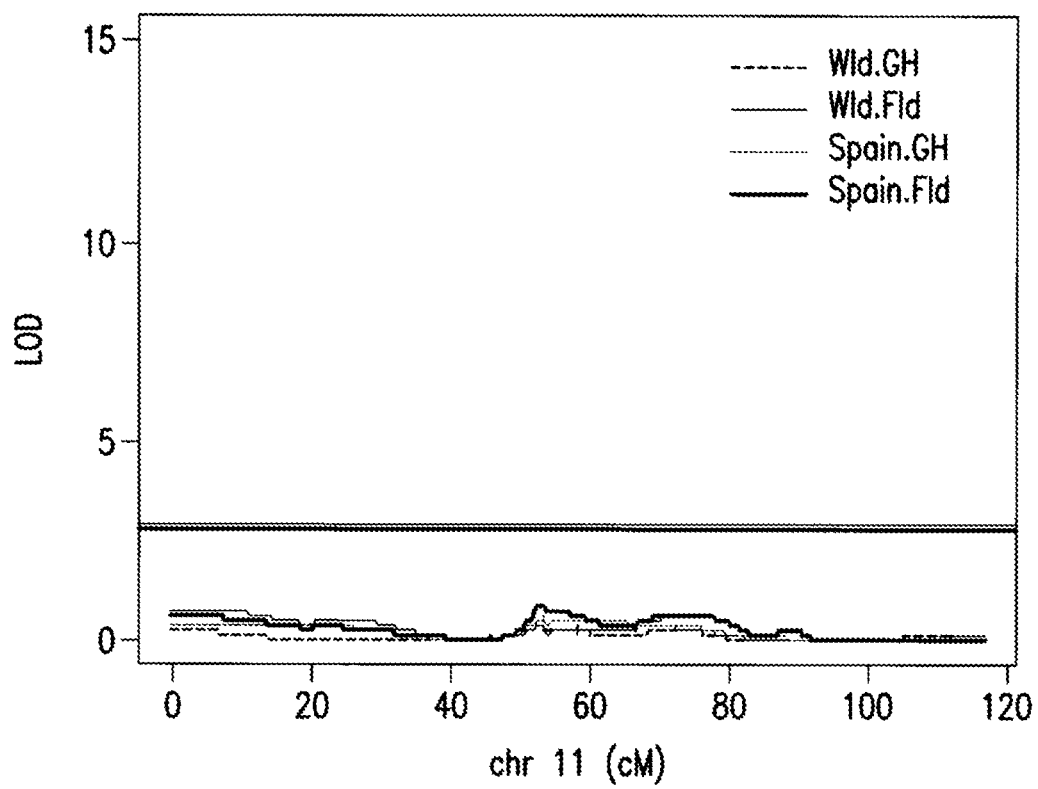
Figure 2:
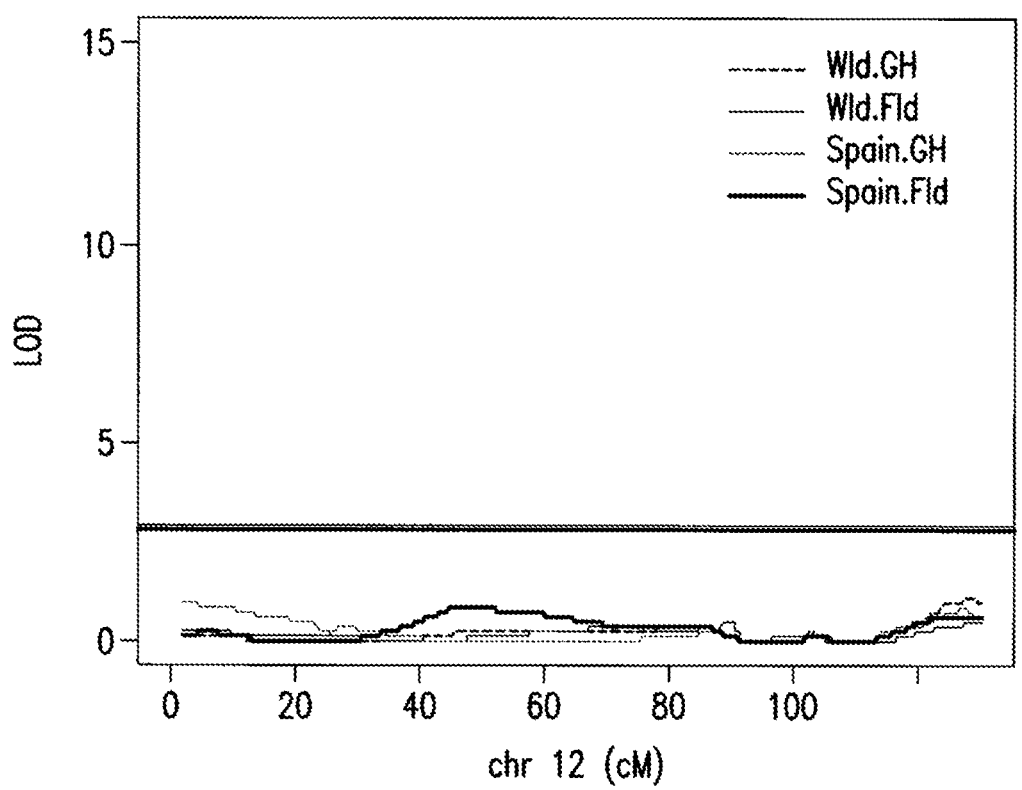

Sequences used for design of genetic markers on chromosome 4.

| SEQ ID NO. | Marker | Pos (cM) | PBC167-derived genotype | Sequence used for marker design |
|---|---|---|---|---|
| 1 | NE0235653 | 7.13060677 | GG | ATACTAAATCCAATAGTGCTCTTCCGCTGAAAGTTCATAA TAGCCTGTAGATTTGAAAGA[A/G]GCAAGAGGTTAATCCA AATGAATTCGCGATGAAAAGCAGAATAAACGAAACCCGG GACTT |
| 2 | NE0236986 | 9.093390743 | TT | AATAATTTATAGCTCCACAAATAGTCGATAAGTGGTTTAG ATCAAAAAGTTGAAAGTCT[T/C]TCTTACACTTTGTGCCA AGTCAAAGGCAGTGGCGGATCTACATACAATTCAAGGGG TTCA |

TABLE 1-continued

Sequences used for design of genetic markers on chromosome 4.

| SEQ ID NO. | Marker | Pos (cM) | PBC167-derived genotype | Sequence used for marker design |
|---|---|---|---|---|
| 3 | NE0236080 | 9.157834477 | GG | AATTCCATTAGAACAGGTTCCATCAGAGCAGCAAAAGATT GTTCAACTATGCAGGCAGCT[A/G]AATAGGCCTGTTATAGT TGCTTCCCAGTTGCTGGAATCTATGATTGAATACCCTATTC CC |
| 4 | NE0239177 | 10.12474833 | AA | CAATTTGCAAGGGAAAATCCAGCCTCCATGATGACTTATC ACAGGTCGTAAACACTGTGT[A/G]GTCAATGTAGAAACTG TAAAAAAAAAAAAAnnCATTAACTAGACAA |
| 5 | NE0238603 | 10.89286968 | CC | GAGATCAAATGATTCAGACAAATAAAGAATACTAAAAGA AAGTAACATACAGTAAGAGA[A/C]ACATGTGAAACAATGT AAGACAATTAAGAGAAGGGTGAGAAAGCCCACCCCTCCA CGTGC |
| 6 | NE0238046 | 11.0627144 | GG | TGAnGTCTTTGGGTAGGAATCCTAAATAGAAATTTGTGCA GTGGAGAAGTACGTCCTGTC[A/G]AAGGAATTGGGAAGTC ACTGAGTGTCGGACAAGTTGTATGGGCTCCATCTGGTGAA GGCT |
| 7 | NE0237823 | 11.56502861 | TT | GTAACTGACGTAAGGGTAGATCCAAGATTTGAACATTATG TATTCGAGTTAGACTTTCTA[T/G]TGTAGTCCATTTGGTTTA TTTATGACTCGAAACCTATTATTTGCACTCETTAGTAAAC A |
| 8 | NE0240044 | 12.04911329 | TT | CGTTCCAAGTACCAACTCATCCACACAGTACGTACACACA AGGGCGTGGATGAAAGGAGC[A/T]ATGGCTGTGTGTTCCG GGAGGAGGAAGAGAAGGAGGAGGTAGGCGTTGCCCTGTC GAAGG |
| 9 | NE0237442 | 13.39042803 | AA | GCCTTCGGAAATCCAAATGTGCCTGGTGCTGGTTATGGTA GCGGTCAAGCTGGTGGATC[A/G]AGAAGCTCGTGGGGTTC TCAGGGTCCTTCTGGATATGGGAACATGGGCTATGGTAAT GCA |
| 10 | NE0238536 | 13.910493 | AA | GTGGTATGGGTGGTGGAAGTTACCAGGGGTATGGTGCATC TGGTGACAATCCCAGTTCTT[A/G]TGACAGAATGGATACC AACAGATACATGCAGTCACAAAACACTGTAGGTGGCTATC CACC |
| 11 | NE0236808 | 14.10971525 | TT | GCCATAGTTAAATAGGTTCTCCTTCTGCTAATGTACATCAT CTATGAAATTTAACATCTG[T/C]ATAATGCAGGTGCCTCCT ACTTTGAGATTTGTGATGGATGGTGAAATGCCCGATTA |
| 12 | NE0238448 | 14.10971525 | GG | CACACAACCGATACTTACTATTnCAGAAAGTCACTTnCTTn GCAACCCTCCGGGGAAGTT[A/G]GTCACTTTGTCAATCAG AAATGCAGAATTTAACCAAGAATACCAAGCGGCCGTTTCC TCA |
| 13 | NE0241383 | 14.10971525 | TT | GATATAGGAGTATCATGGAAGTTGTGCCCTTTGATATGGT ATGCGTGGAACCATTTGATC[T/C]ACATTTGTCCAGTTTAT GCTCTAAGTCCCAGCATATCTTAGCAATAGCAGCCCTGTT ACA |
| 14 | NE0240496 | 14.78769275 | CT | CTATTGGGAAGCCTCCCACCAAACATATGTTCTATCTTAC CCAACGTTGAAAGCGTTTAT[T/C]TGGCCTATACCAATTTT GCTGGGACTATTCCTCATTCCATC |
| 15 | NE0237841 | 16.76424258 | GG | ACAGAATTGGTAGCCTTGATCACCCnGCTTCGGGTCCTGG TGACATGGTGGAACATTTGC[A/G]GCCAGAAACTGAGTCA TTTACTGAGGTTTTACTTGCAAAGTTTGTCCGAATGCTCCA GAA |
| 16 | NE0239164 | 18.19035298 | AA | TGACCTTTATAGTnnAAAAAAAnTTAAAnGGACAAGAAA TGGAAAGGGAACAAAGAAGA[A/G]TATCAGCAGCTTATCT ATGTTTAACAAATTATGACCTCCATTAGCTTTTATATTAAT AAA |
| 17 | NE0236790 | 21.56183958 | GG | CGATACATGCGCACCACTCGACATCTTTTGTGGTTCTCAA GATAACAATCGCAGGTAACA[T/G]CATCTGTAAATCCAAT AGAACAACTTGGnGGTAATAATATTCCCTnAGAACACCCA AGCA |
| 18 | NE0238624 | 21.56183958 | GG | TGGAATCAAGGGTCAGGAAGACTGAAATGTTGTATGCCG AAGGTCGTCAGCTGAAAGTGA[A/G]TCTAAGTCTTTTAATA |

TABLE 1-continued

Sequences used for design of genetic markers on chromosome 4.

| SEQ ID NO. | Marker | Pos (cM) | PBC167-derived genotype | Sequence used for marker design |
|---|---|---|---|---|
| | | | | CTTAGAAAAATTTTCATACTTTTCAAGACTAAGTGCACTCTACT |
| 19 | NE0240275 | 21.56183958 | GG | CnGGGTTGGGGnAAGGGCTGAATCTTATAGTTCTTTCTGTGTGTCAAGTTAACGCCTCGT[A/G]GAGTCACTTACGATCTCTTCGTTTCCATTTTTCTTCTTGTTAAAGAATGAAnTTGGGTCT |
| 20 | NE0238899 | 24.87135151 | GG | AAAATTGCCTTAGTACGAATTAATACTCTTATATATTCTCAAAAGACATATACCCAGACC[A/G]TACTTGTGGGATTACACCGGCTATGTTGTGGTTGTTTTGTGAAGACATATTTAAGTACTC |
| 21 | NE0238734 | 24.87248992 | GG | GTTAAGCTTCTGTGAAGCCAAAAGTnTTTTTTTnnCGAAGTGTTTAGTTAAAAAAGTTGC[A/G]TTGTTTGGCCAAGCTTTTAGGAAAAAGATAAGTATTTCGAGTCGTTGTAGAAACTGCACT |
| 22 | NE0240256 | 25.1081287 | CC | CTGTTCAAGAGCAATTCAGTCATTTGTTCTTCAGGTAATCTTGTTTATTCCCAAATTGTG[C/G]CAATCAATTTGGTTCTCATCATTGGTATCAGAGACCTAATCATCTGACCTGTGCGATGG |
| 23 | NE0237985 | 25.17303092 | CC | TACACnGGTAAAACTGACAAGGCATCAGCGTTAGCCAATAATGAACTTTTAGCGCGGAAC[T/C]TCAAGTGACCAAGTGCATGAAACCAAATCAAGAAGGTAAAGATATGnTGATCACCTGAAT |
| 24 | NE0239638 | 25.88460917 | GG | TGGATATAGGAAAGATCACTTAGAAATTCAACAATCTTTTTCGTCTTTAAGAGCCTGTAG[A/G]CTTCTTTAGCATCTACACATCAAAATTCTCCAGACATTTCAAATTATATACAGTCCACGA |
| 25 | NE0239147 | 26.81001479 | CC | ACTCTTTTATTCGTAATGTTCATAGACGAAAGAGACGATCCTTCGCTCCTGTGAGCAGGA[T/C]GGTGTTCCAATGTGCAAGGCCCTTTCCTGAAGAGGTCGAAAATTCACGACCCATTCATAG |
| 26 | NE0240589 | 29.49618369 | GG | TAAGTACAAGTTTAAGGATTCAAGTTATCTCTTAAATTAGCTTTCAGAACATGATGACAT[T/G]CTTTCTGCTTTGCGATGGGACAGATGGAATAnTCAAGTCATGTTGACTTGAT |
| 27 | NE0237975 | 30.80785657 | GG | AATAATGACATTCGATTTGTCAGCAACTAAATCAAAGCACTCCATCAAGCAACAATAAGA[T/G]ATCCGGACTTTCATCCGCATGCACCCTCACAGCAAGAAAGTTCCCCATACTACTTACACT |
| 28 | NE0239291 | 31.51094171 | AA | GTTTTTCCAATGTATCCACCAAATACAGTCATGCCTTTTGTATATTGGGATCAACCTA[A/G]TGTGTTCGCGCCAGTTCATTATCGCTCTTCTTATAGATGTATCGCACCTGGAAGTTGCAT |
| 29 | NE0238449 | 34.38657122 | TT | CTTTTTCTCTTATTnCCTTTTnATTTTCTTGTTTTGCTACTAAAAGCTTGAAGTTCTATT[T/G]TGCAATGTGCATACTTGCTTGAAGTCTCGTATTCACATGTTAAGACCTTCTCTTTAGAAA |
| 30 | NE0239990 | 34.8438471 | CC | CTTAGATCAAAAGTGAATACAACAAAAnGTTACCGGATGATTCCATTTCTAAGCCGACCA[T/C]ATCCACAGTAAACCCATATGTAGCAAGATAGAAATTGAAAACAATTATCACCGTACACAT |
| 31 | NE0231151 | 37.40944245 | CT | GCGCCCACGAACATTGCCGTGTTGGGAGTTACCAAGAGGCTGATGCAGAATGTACAAAGT[T/C]GTCTGCAATACGACACGTATGGTTTTGGAGACATTCCTTATTTGGTAACGOGGAGAGAA |
| 32 | NE0240438 | 37.57094558 | CC | CTCGTCTTCTTTCTTGATCTTTTAAGCACCGCGTTGATGAAATTTTTCGTGTTTTGCTTA[T/C]ACGAGTTGCATTTTTGAAATAATGTTAGTACGTTTTCAGATTATGATCATAGACTTCAAA |
| 33 | NE0237121 | 38.23427336 | AA | AATAGATCAAATCAACAATGGAGTTTAATTGAGAAAAAGAAGAAGCCAATAACAGATATC[A/G]CACAAATTTGGATTAGAATCGAGnAGAATGAGnACATAGATCACACnAATTCCTCAGAAT |

TABLE 1-continued

Sequences used for design of genetic markers on chromosome 4.

| SEQ ID NO. | Marker | Pos (cM) | PBC167-derived genotype | Sequence used for marker design |
|---|---|---|---|---|
| 34 | NE0238426 | 38.41163895 | TT | GGGGCGGAGCTAGAGTTGTAGTTACGGATTTAGCAGAAC GAATGACACTTCTATAGGGCT[T/C]AAGTAGTTGGAATGA ATCAGTTACTACTGATCAAAGTTATCAAAAGTTTTCGTATT GTCT |
| 35 | NE0235272 | 39.78935972 | TT | CTTAAGAACACTCCCACTTCGGCTTAAGCACCATCGAAAA GACAAACTAGAACCAGCTCA[T/C]GCATACAATAAAAAGC ATACACAAAAGTTACGAACCATAATTGGTCGTAAAATGG AGCAG |
| 36 | NE0237901 | 39.88201323 | TT | TCTTGGAAAATCGATATCAGAAATGGAAATCCCATCGGGC TGTCAGGAGTTGACTCTTAG[T/C]TATCTTTGTGAAAGTTC CAAAnTGGGGTTTGGAGAGAGAGATGTTTTCGTGGATAAA GGT |
| 37 | NE0237351 | 40.28912425 | TT | CTTAAGAACACTCCCACTTCGGCTTAAGCACCATCGAAAA GACAAACTAGAACCAGCTCA[T/C]GCATACAATAAAAnGC ATACACAAAAGTTACGAACCATAATTGGTCGTAAAATGG AGCAG |
| 38 | NE0241057 | 42.60970639 | CC | CTTTATCGATGATTATCTGCTCTGGAGGTGTACGTTTCTCA ACAGTTTCTATACTTGCAA[T/C]AGTTAGGCTTGATGTTGT TAAAGCCTAACTACTCGCAAACACACTCAGAACCAAATGC AA |
| 39 | NE0237348 | 45.2687706 | TT | ATCGGCATCCTCAAGACTATCCATTGTTATAAAAGCAAAA CCACGAGAGATACGAGAACG[T/C]GGCTCCACAACCAAGA AAGCTGATTTnACCTGGTCGACAGAAAGTAAAnGAAAAAn CTCA |
| 40 | NE0240958 | 45.2687706 | CC | CAGATATTTTCAGTAAAATCGTAATTAGATCCTTGAGATC TAACTGCACTCTAATGTCAC[T/C]TCAGGAGGCAAAACCA AAGAAGATTTTTTCTTCCAGCTCCATTAACTAAACCGCAT ACTC |
| 41 | NCANN005704058 | 21.56184 | GG | CAACCATCCCTCAACTAACGTGGGACACTTAACAATCTAC CGCACACCCAGGCCCGCCTACTAGAGCGTGGACGAAATA ATGAGGGCCCTACATGGAGACGCACNGTAAGAGGGATGA GTCTGGCTCTGACCATGTGNNTAANTCAATCCTAAAAGCT ATCTCATGAAGTGAGGATTGACCACNACCATACAAC[G/A] AGCTACAAACAAGCCATCCCTCAACCAATATGGGACATTA AACACTTCTTAAGTTCCAACTTANAAGTGTTGTCTTGAAG GATTGAGCAAGTGTCAA |
| 42 | NCANN005704056 | 25.88461 | CC | ATGCATGAGGGCAATACAAGCNTTGAATCGAAATGACTG TTTAATCTCGTGGACTGTATATAATTTGAAATGTCTGGAG AATTTTGATGTGTAGATGCTAAAGAAGNCTACAGGCTC[C/ T]AAAGACGAAAAGATTGTTGAATTTCTAAGTGATCTTT CCTATATCCACCCCTAAGCTGCCAGCGCTGGGGGTTCCTT TCTCTTGGTTGGCCTTCCTAG |
| 43 | NCANN005704052 | 29.49618 | CC | CCGTTTTAACATATGTACATGGCTTGTCTTAGTTACTAATA TCATCTGATACCATGTGCAAACATGACTTGGGAATGTGGG ACTTAATATACTTGTAACC[C/A]TGTGTTTTGTTATTGAAA TTAAAGTTCAGTGTTATGTTTGTTTAAAACGGCCACTNGG TACATGTTATACNGCTCTTGGTCTAAGCTCTTATCTACATA CTATAAATAACTTTTTTTGTTCTTGGTTTCTATCACCAATT ATTATTTTATC |
| 44 | NCANN005704049 | 31.51094 | TT | ATTTCTGGATTTCTACTTGTAAAAGGGAAGCCCGOTGCAC TAAAGCGCCCGTTATGCAAGGGGGCCGGGGAAGGTTCAG CCTGCAACGGTCCATTGTACG[T/C]AGCCTTANCCTGCATT TCTNCAAGAGGCTGTTTCCACAGCTTGAATCCGTGACCTC CTGGTCACATGGCAACAACTTTACCCA |

Where n = A, C, T, or G.

DETAILED DESCRIPTION OF THE INVENTION

The invention provides methods for identifying pepper plants, of the genus *Capsicum*, having resistance or increased resistance to Powdery Mildew caused by the fungus *Leveillula taurica*. Such pepper lines can be referred to as Powdery Mildew resistant pepper varieties. Methods of breeding Powdery Mildew resistant pepper lines are further provided. Also disclosed herein are molecular markers that are linked to quantitative trait loci (QTL) contributing to Powdery Mildew resistance. Through use of the markers, one of skill in the art may increase the degree of Powdery Mildew resistance in pepper or select plants for an increased predisposition for Powdery Mildew resistance. In particular embodiments, the methods are performed on progeny pepper plants of pepper line PBC167, such as members of the PBC167×SBY 99-1179 mapping population disclosed herein, or progeny thereof. The QTL identified in this manner may be combined with one or more other QTL that also contribute to Powdery Mildew resistance, as desired. A QTL was identified here which corresponds to the location between approximately 7 to 45 centiMorgans (cM) on pepper chromosome 4 and is flanked by markers NE0235653 and NE0240958 and which has a significant effect on Powdery Mildew resistance in pepper. This QTL significantly reduces a plant's Powdery Mildew disease rating in a Powdery Mildew pathology test as described herein, for instance in the PBC167×SBY 99-1179 mapping population genetic background, when grown in multiple tested geographic locations.

The definition of this QTL allows the use of specific molecular markers, such as those disclosed herein, in a plant breeding program to introgress a Powdery Mildew resistance trait to agronomically elite pepper lines. It also allows movement of the trait within agronomically elite pepper lines. Marker-assisted introgression involves the transfer of a chromosomal region, defined by one or more markers, from one germplasm to a second germplasm. An initial step in that process is the localization of the trait by mapping, which is the process of determining the position of a genetic element relative to other genetic elements and genetic markers through linkage analysis. The basic principle for linkage mapping is that the closer together two features are on the chromosome, the more likely they are to be inherited together. Briefly, a cross is made between two genetically compatible but divergent parents relative to a trait under study (e.g. Powdery Mildew resistance). Morphological, genetic or molecular markers are then used to follow the segregation of traits under study in the progeny from the cross, often termed a "mapping population." The current invention relates to the introgression in a pepper of a chromosomal region, e.g., a mapped QTL, which is capable of causing a plant to be more resistant to the onset and progression of pathogen-induced disease symptoms caused by *Leveillula taurica*. The inventors identified a chromosomal region responsible for Powdery Mildew resistance and used marker assisted breeding to introgress these specific linkage blocks into other pepper germplasm that lacked such resistance to Powdery Mildew. In certain embodiments of the invention, the process for producing a Powdery Mildew resistant pepper plant or line comprises introgressing at least one chromosomal locus mapping to chromosome 4 from a more Powdery Mildew resistant pepper plant, line, or variety into a less Powdery Mildew resistant pepper plant, line, or variety. In specific embodiments, the more Powdery Mildew resistant pepper plant, line, or variety is PBC167, or a progeny plant thereof containing the disease resistant trait.

Introgression of a particular chromosomal region or set of regions into a plant genotype is defined, for example, as the result of the process of backcross conversion. Additional examples of breeding techniques intended to reach the same result include pedigree selection and dihaploidization of an F1. A plant genotype into which a DNA sequence has been introgressed may be referred to as a converted genotype, line, or variety. Such genotype, line, or variety may be an inbred or a hybrid genotype, line, or variety. Similarly a plant genotype lacking said desired DNA sequence may be referred to as an unconverted genotype, line, or variety. During breeding, the genetic markers linked to enhanced Powdery Mildew resistance may be used to assist in breeding for the purpose of producing pepper plants with increased resistance to *Leveillula taurica*. A skilled worker would understand that the introgression of a Powdery Mildew resistance trait into a pepper plant may be monitored by visual clues such as by use of a disease resistance test with a disease rating scale as described herein, or by monitoring and breeding for the presence of molecular markers as described herein (i.e. marker assisted selection), or both.

Localization of such markers to specific genomic regions further allows for use of associated sequences in breeding and to develop additional linked genetic markers. It will be understood to those of skill in the art that other markers or probes which more closely map the chromosomal region as identified herein could be employed to identify plants comprising a desired QTL for Powdery Mildew resistance. The chromosomal region of the present invention facilitates introgression of increased Powdery Mildew resistance from Powdery Mildew resistant germplasm, such as PBC167 or progeny thereof, into other germplasm, preferably agronomically useful pepper germplasm. Linkage blocks of various sizes could be transferred within the scope of this invention as long as the chromosomal region enhances the Powdery Mildew resistance of a desirable pepper plant, line, or variety. Accordingly, it is emphasized that the present invention may be practiced using any molecular markers that genetically map within the identified region, provided that the markers are polymorphic between the parents.

In particular embodiments, these markers may be genetically linked to the described QTL for Powdery Mildew resistance which is located on pepper chromosome 4, for instance as defined in the genetic map of Wu et al. (*Theor. Appl. Genet.*, 2009, 118(7):1279-93). In certain embodiments, the markers are within 50 cM, 45 cM, 40 cM, 35 cM, 30 cM, 25 cM, 20 cM, 15 cM, 10 cM, 5 cM, 3 cM, 1 cM, or less, of the QTL defined on chromosome 4, at 7.7-42.7 cM based on analysis of the PBC167×SBY 99-1179 mapping population as described herein. In particular embodiments, the markers used to follow the presence of the QTL for Powdery Mildew resistance which is located on pepper chromosome 4 are selected from the group consisting of: NE0235653, NE0238847, NE0237736, NE0236986, NE0236080, NE0237755, NE0239177, NE0238603, NE0238046, NE0237823, NE0230886, NE0240044, NE0237442, NE0238362, NE0238536, NE0236808, NE0238448, NE0241383, NE0240496, NE0237841, NE0239164, NE0240741, NE0236790, NE0238624, NE0240275, NE0238899, NE0238734, NE0240256, NE0237985, NE0239638, NE0239147, NE0240589, NE0237975, NE0239291, NE0235654, NE0238449, NE0240786, NE0239990, NE0231151, NE0240438, NE0237121, NE0238426, NE0235272, NE0237901, NE0237351, NE0241057, NE0237348, NE0240958, NCANN005704058, NCANN005704056, NCANN005704052, NCANN005704049, or other genetic markers linked to the QTL. The associated presence of alleles conferring resistance to Powdery Mildew may be identified by use of well known techniques, such as by nucleic acid detection methods utilizing probes or primers comprising a sequence selected from the group consisting of SEQ ID NOs:1-44. In certain embodiments, the method comprises detecting the presence of one or more single nucleotide polymorphisms (SNPs) given in one or more of SEQ ID NOs:1-44.

In certain embodiments, the Powdery Mildew resistance QTL of chromosome 4 is defined as spanning the region defined by SNP marker NE0235653 (map position 7.131 according to Table 7), to SNP marker NE0240958 (map position 45.269 according to Table 7).

The Powdery Mildew resistance QTL of the present invention has been defined in a mapping population based on a cross of pepper lines PBC167 and SBY 99-1179, as being located between genetic markers NE0235653 and NE0240958, at about 7 cM-45 cM in the linkage group, and as defined by analysis of that mapping population (e.g. see Table 3). Further, one of skill in the art would understand that assignment of such genetic map positions may be affected by the mapping population being analyzed, including for instance the parent lines used, the marker density, and the size of the population, each of which may affect the level of recombination which is seen, and thus the assigned genetic map position. An integrated genetic and physical map may be utilized to define the position of a pepper QTL, such as one provided by Wu et al. (*Theor. Appl. Genet.*, 2009, 118(7):1279-93), for instance relative to markers with known genetic and/or physical map positions.

As used herein, a "hybrid pepper plant" includes a plant resulting directly or indirectly from crosses between populations, breeds or cultivars within the genus *Capsicum*. "Hybrid pepper plant" as used herein also refers to plants resulting directly or indirectly from crosses between different species, varieties or genotypes.

As used herein, a "female parent" refers to a pepper plant that is the recipient of pollen from a male donor line, which pollen successfully pollinates an egg. A female parent can be any pepper plant that is the recipient of pollen. Such female parents can be male sterile, for example, because of genic male sterility, cytoplasmic male sterility, or because they have been subject to manual emasculation of the stamens. Genic or cytoplasmic male sterility can be manifested in different manners, such as sterile pollen, malformed or stamenless flowers, positional sterility, and functional sterility.

As used herein, an "agronomically elite plant" refers to a genotype that has a culmination of distinguishable and desirable agronomic traits which allow a producer to harvest a product of commercial significance.

As used herein, "cytoplasmic male sterility" refers to plants that are not usually capable of breeding from self-pollination, but are capable of breeding from cross-pollination.

As used herein, a "part of the pepper plant" is further defined as pollen, an ovule, a leaf, an embryo, a root, a root tip, an anther, a flower, a fruit, a stem, a shoot, a seed, a protoplast, a cell, and a callus.

As used herein, "improved resistance" refers to a more resistant pepper plant score on a Powdery Mildew bioassay rating scale as compared to a control pepper plant with a similar genetic background but lacking the claimed QTL region.

As used herein, "linkage" is a phenomenon wherein alleles on the same chromosome tend to segregate together more often than expected by chance if their transmission was independent.

As used herein, a "marker" is an indicator for the presence of at least one phenotype, genotype, or polymorphism. Markers include, but are not limited to, single nucleotide polymorphisms (SNPs), cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A marker is preferably inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with Powdery Mildew resistance. Stringent conditions for hybridization of a nucleic acid probe or primer to a marker sequence or a sequence flanking a marker sequence refers, for instance, to nucleic acid hybridization conditions of 5×SSC, 50% formamide, and 42° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies, and nucleic acid sequencing technologies, including whole genome sequencing, etc.

As used herein, a "desirable trait" or "desirable traits" that may be introduced into Powdery Mildew resistant pepper plants by breeding may be directed to the pepper fruit or the pepper plant. Desirable traits to be introduced into pepper plants and pepper fruit may be independently selected. Desirable pepper fruit traits, e.g. as displayed by agronomically elite lines or cultivars, and that may be independently selected include, but are not limited to: fruit size, shape, color, surface appearance; seed number, seed size, locule number; pericarp thickness and toughness; taste and shelf life. Desirable pepper plant traits, e.g. as displayed by agronomically elite lines or cultivars, and that may be independently selected include, but are not limited to: plant vigor, leaf shape, leaf length, leaf color, leaf number, plant height, whether the plant is determinate or not, time to maturity, adaptation to field growth, adaptation to greenhouse growth, and resistance to one or more diseases or disease causing organisms. Improvement in such trait may be assessed by comparison with one or more other pepper lines, including a parental line. Any combination of desirable pepper fruit traits, pepper plant traits, or pepper plant and fruit traits may be combined with a Powdery Mildew resistance trait.

As used herein, "polymorphism" means the presence of one or more variations of a nucleic acid sequence at one or more loci in a population of one or more individuals. The variation may comprise but is not limited to one or more base changes, the insertion of one or more nucleotides or the deletion of one or more nucleotides. A polymorphism may arise from random processes in nucleic acid replication, through mutagenesis, as a result of mobile genomic elements, from copy number variation and during the process of meiosis, such as unequal crossing over, genome duplication and chromosome breaks and fusions. The variation can be commonly found, or may exist at low frequency within a population, the former having greater utility in general plant breeding and the latter may be associated with rare but important phenotypic variation. Useful polymorphisms may include single nucleotide polymorphisms (SNPs), insertions or deletions in DNA sequence (INDELs), simple sequence repeats of DNA sequence (SSRs) a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, dsRNA, a transcriptional profile, and a methylation pattern may comprise polymorphisms. In addition, the presence, absence, or variation in copy number of the preceding may comprise a polymorphism.

As used herein, "genotype" is the actual nucleic acid sequence in an individual plant. As used herein, "phenotype" means the detectable characteristics (e.g. level of Powdery Mildew resistance) of a cell or organism which can be influenced by genotype.

As used herein, a "quantitative trait locus (QTL)" is a region of DNA that is associated with a particular phenotypic trait.

Powdery Mildew resistance of a pepper plant provided herein can potentially be defined as complete resistance or partial resistance. The Powdery Mildew resistance of a pepper plant provided herein can be measured by any means available in the art.

In one aspect, Powdery Mildew resistance of a pepper plant is determined by using a disease rating of percent leaf coverage of Powdery Mildew spores developed after inoculation or infection with Powdery Mildew on pepper leaves using a scale of symptoms of 0%, 10%, 20%, 30%, 40%, 50%, 60%, 70%, 80% and greater than about 90% sporulation covering the leaf area. A disease rating of 0% indicates a completely resistant plant.

In another aspect, Powdery Mildew resistance is determined by obtaining disease ratings of spore development after one or more rounds of inoculation or infection with Powdery Mildew on pepper leaves and/or seedlings.

Resistance may be scored on an exemplary three point scale (where 1 is resistant and 9 is susceptible) as follows:
1=(High Resistance): No sporulation
5=(Intermediate Resistance): Very light sporulation usually underneath the leaf
9=(Susceptible): White sporulation on the whole surface of inoculated leaves Resistance may also be scored on an exemplary 5 point scale (where 1 is resistant and 5 is susceptible) as follows:

| Density sporulation: | Spot per leaf: |
|---|---|
| 0 = no visible sporulation | 0 = No spots |
| 1 = few spores per spot, <10% | 1 = 1 or 2 spots |
| 2 = light sporulation, 25% | 2 = 3, 4 or 5 spots |
| 3 = strong sporulation, easy to see 25-50% | 3 = more than 5 spots per leaf |
| 4 = very strong sporulation 50-75% | 4 = 50% of leaf affected |
| 5 = sporulation on upper and lower side of leaf | 5 = 90% of leaf affected |

Sporulation refers to the presence of visible powdery, white growth on leaf surfaces. As described here, this may be measured by visual perception of the percent of leaf area affected. Tests are evaluated once symptoms have developed on susceptible checks. PBC167 may be used as a "resistant" control. Scores of 1-5 or 1-9 indicate varying levels of resistance or susceptibility. On the 1-5 scale, a score of 1-2 after one or more rounds of inoculation or infection, and preferably two or more rounds of infection, indicates a resistant plant; a score of 3 after one or more rounds of inoculation or infection, preferably two or more rounds of infection, indicates a plant exhibiting intermediate resistance; a score of 4-5 indicates a susceptible plant.

Pepper lines having Powdery Mildew resistance, or partial resistance, demonstrate a reduced level of symptoms relative to a non-resistant control pepper line after inoculation or infection with Powdery Mildew. The level of symptoms can be used as an indicator of Powdery Mildew resistance. Disease symptoms measured can be any disease symptoms associated with Powdery Mildew infection. Symptoms can include the presence of white or brown sporulation patches on the underside of leaves, leaf yellowing or development of light-green to bright-yellow blotches that later turn necrotic on the upper sides of leaves, curling of infected leaves, general leaf chlorosis or leaf drop. In one aspect, a Powdery Mildew resistant pepper line demonstrates a reduction of sporulation patches of at least, or greater than, 10%, 20%, 25%, 30%, 40%, 50%, 60%, 70%, 75%, 80%, 85%, 90%, 95%, or 98% relative to a non-resistant control pepper line. In other aspects, the leaves of a Powdery Mildew resistant pepper plant demonstrate less than 15%, or less than 10%, or less than 5%, or less than 2% symptomatic area when exposed to Powdery Mildew. In another aspect, the pepper plant belongs to a pepper variety or cultivar, and in another aspect, the pepper plant is an inbred pepper plant.

In another aspect, the pepper plants and varieties provided herein demonstrate little or no symptoms of sporulation after inoculation or infection with Powdery Mildew. In some aspects, a Powdery Mildew resistant pepper plant demonstrates symptoms of sporulation on less than 25%, 20%, 15%, 10%, 9%, 8%, 7%, 6%, 5%, 4%, 3% 2%, or 1% of the pepper leaf surface.

Powdery Mildew resistant pepper plants may exhibit a delay in the onset of symptoms of Powdery Mildew sporulation relative to a non-resistant control pepper plant. In some embodiments, the Powdery Mildew resistant pepper plants exhibit a delay of 1, 2, 3, 4, 5, 6, 7, 8, 9, 10, 11, 12, 13, 14, or more days in the onset of symptoms of Powdery Mildew sporulation relative to a control pepper plant. In other embodiments, the Powdery Mildew resistant pepper plants exhibit a delay of at least 7 or more days, 10 or more days, or 14 or more days in the onset of symptoms of Powdery Mildew sporulation relative to a control pepper plant.

In one aspect, the pepper plant is a seedling at the time of inoculation or infection. In some aspects, the pepper plant is a seedling at the 4, 5, 6, 7, or 8 leaf stage of development when inoculated. In one aspect, disease symptoms can be measured at any time after pathogenic challenge of a pepper plant. In other aspects, symptoms can be measured 2, 3, 4, 5, 6, 7, 8, 9, 10, 11, 12, 13, 14, 15, 16, 17, 18, 19, 20, 21, or more days after inoculation. In another aspect, the pepper plant is any age of plant at the time of inoculation or infection.

In another aspect, disease symptoms can be observed after Powdery Mildew challenge of an entire plant or a part thereof, for example, a plant cutting. Powdery Mildew resistant pepper plants of the present invention may exhibit an increase in fruit yield after inoculation or infection with Powdery Mildew relative to a control pepper plant inoculated with Powdery Mildew. In one aspect, the resistant pepper plants exhibit a 2%, 5%, 10%, 15%, 20% or more increase in fruit yield, based upon the total mass, number, or total volume of fruit, relative to a control pepper plant after one or more rounds of inoculation or infection with Powdery Mildew.

The present invention provides for and includes pepper plants that exhibit resistance to one or more isolates or races of Powdery Mildew. In some embodiments, the pepper plants of the present invention exhibit resistance to 1, 2, 3, 4, 5, 6, 7, 8, 9, 10, or more isolates or races of Powdery Mildew.

The present invention provides for a seed of a pepper plant capable of producing a plant having Powdery Mildew resistance. In one aspect, the pepper plant can be an open-pollinated variety, a hybrid parent inbred line, or a male sterile line. In another aspect, the invention provides seed of a pepper plant capable of producing a hybrid pepper plant having Powdery Mildew resistance.

The pepper plants of the present invention can be pepper lines adapted for greenhouse pepper production or for field pepper production. In one aspect, the pepper plants of the present invention are adapted for greenhouse pepper production.

The present invention also provides a hybrid pepper having Powdery Mildew resistance. In another aspect, the present invention provides a hybrid pepper exhibiting Powdery Mildew resistance after inoculation or infection with Powdery Mildew.

Agronomically elite pepper plants represent one aspect of the present invention. In one aspect, certain pepper agronomic traits, including, for example, fruit size, shape, color, weight, pungency, taste and fruit yield may be important to the commercial value of the crop. Fruit size and shape, may be of particular interest if the peppers are grown for processing such as pickling. The present invention provides for a pepper plant having one or more traits selected from the group consisting of:

a. plants with prostrate, compact, erect growth habits;
b. plants that have glabrous stems or have sparse, intermediate or abundant stem *pubescens;*
c. plants that have glabrous leaves or have sparse, intermediate or abundant leaf *pubescens;*
d. plants with green or purple stems;
e. plants that have pendant, intermediate, or erect pedicle position at anthesis;
f. plants that have white, green-white, lavender, blue or violet corolla color;
g. plants with yellow, pale blue, blue, or purple anthers;
h. plants with white or blue filament colors;
i. plants having a stigma included within the anthers, at the same level as the anthers, or exerted beyond the anthers at full anthesis;
j. plants that are male sterile or male fertile;
k. plants that have low, intermediate or high fruit set;
l. plants with white, straw or cream, yellow, brown, dark brown, or black seeds;
m. plants that have smooth, intermediate, or dentate calyx margins;
n. plants that have or lack an annular constriction at the junction of the calyx and peduncle;
o. plants that have declining, intermediate, or erect fruit position;
p. plants that have white, green, yellow, orange, red, purple, brown, or black immature fruit;
q. plants that have white, green, yellow, orange, red, purple, brown, or black mature fruit;
r. plants with pepper fruit that is sweet, or has low (i.e. mild), intermediate (i.e. medium) or high (i.e. hot or very hot) pungency;
s. plants that have an average fruit length at ripeness that is very short (less than about one cm), short (about 5 cm or about 2 to about 7 cm), medium (about 10 cm or about 7 to about 12 cm), long (about 15 cm or about 13 to about 25 cm) or very long (greater than 25 cm or about 25 cm to about 40 cm);
t. plants with a fruit wall thickness (measured halfway between the point of attachment of the stem and the blossom end) from about 0.5 to 1.5 mm or from about 1 to about 2.5 mm or from about 1.5 to about 4 mm or from about 2 to about 5 mm, or from about 3 to about 6 mm, or from about 3.5 mm to about 7.5 mm;
u. plants that have an average fruit width at ripeness that is about 0.3 to 1 cm, about 1 to 2 cm, about 2 to 4 cm, about 3 to 7, about 6 to 10, about 7 to 11 or greater than about 11 cm;
v. plants without persistent fruit or plants with persistent fruit (fruit that persists and maintains an attachment to the plant after ripening);
w. plants with pepper fruit having an average weight a ripeness from about 1 to 5 g, 5 to 25 g, 25 to 50 g, 50 to 100 g, 100 to 250 g, 150 to 450 g, 200 to 500 g or 300 to 550 g.
x. plants with pepper fruit that is elongate, oblate, round, conical or pointed, campanulate, or bell/blocky;
y. plants where the pepper fruit shape at the point of attachment is acute, obtuse, truncate, cordate, or lobate;
z. plants where the pepper fruit has or lacks a neck at the base of the fruit;
aa. plants where the blossom end is pointed, blunt, or sunken;
bb. plants where the pepper fruit has a smooth, slightly corrugated, intermediate, or very corrugated cross section;
cc. plants with resistance to one or more multi-cellular pests (e.g., nematodes and aphids);
dd. plants with resistance to diseases caused by one or more bacteria or fungi (e.g., *Xanthomonas* sp. and *Leveillula taurica*);
ee. plants with resistance to diseases caused by one or more viruses (e.g., geminivirus, tobamovirus);
ff. plants having or lacking anthocyanins in unripe pepper fruit;
gg. plants having or lacking anthocyanins in ripe pepper fruit;
hh. plants that are resistant or susceptible to low temperature;
ii. plants that are resistant or susceptible to high temperature;
jj. plants that are resistant or susceptible to drought;
kk. plants that are resistant or susceptible to high soil moisture;
ll. plants that are resistant or susceptible to high humidity; and
mm. plants that shed fruit easily or do not shed fruit easily.

In some aspects, a pepper plant of the present invention may produce a pepper fruit having a weight at harvest of about or greater than about 1, 50, 100, 150, 200, 250, 300, 350, 400, 450, 500, 550, 600, 650, 700, 750, 800, 850, 900, 950, and 1000 grams. In other aspects, a pepper plant of the present invention produces a pepper fruit having a weight at harvest between about 1 and about 1000 grams, about 100 and about 900 grams, about 200 and about 800 grams, about 300 and about 700 grams, or between about 400 and about 600 grams. Fruit weight is measured by weighing individual pepper fruit on a scale.

A pepper fruit attribute such as shape, weight, or size can be measured or evaluated at a variety of times. In one aspect, an attribute is measured following growth in a growth chamber. In another aspect, an attribute is measured at the time of harvest. In yet another aspect, an attribute is measured after storage of the pepper fruit at ambient conditions for one day, two days, three days, four days, five days, six days, seven days, eight days, nine days, ten days, eleven days, twelve days, thirteen days, two weeks, three weeks, four weeks, or five weeks after harvest.

In one embodiment, a pepper fruit from a pepper plant having Powdery Mildew resistance has an overall fruit quality rating of 1, 3, 5, 7, or 9, where fruit quality is measured by visual inspection, with a scale ranging from 1=excellent through 9=poor: Rating 1=Excellent; 3=Above average; 5=Average; 7=Below average; 9=Poor; compared to an appropriate commercial hybrid comparison grown in the area. Fruit quality includes, but is not limited to, fruit color, fruit shape, fruit length and diameter.

A further aspect of the invention relates to tissue cultures of the pepper plants described herein. As used herein, the term "tissue culture" indicates a composition comprising isolated cells of one or more types, or a collection of such cells organized into parts of a plant. Tissue culture includes, but is not limited to, compositions comprising protoplasts and calli. Tissue culture also includes, but is not limited to, compositions comprising plant cells that are present in intact plant tissues, or parts of plants, such as embryo, leaf, peduncle, pedicel, anther, meristem, tip and segments of root, stump and stem, explants, and the like. In one aspect, a tissue culture comprises embryos, protoplasts, meristematic cells, pollen, leaves, anthers or cells derived from immature tissues of these plant parts. Means for preparing and maintaining plant tissue cultures are well known in the art. Examples of processes of tissue culturing and regeneration of pepper are described in, for example, Fillatti et al., 1987 (*Bio/Technology* 5:726-730). In some aspects, tissue culture of the pepper plants described herein relates to the culture of protoplasts, calli, or plant cells, that are isolated from, or present in, intact parts of the Powdery Mildew resistant plants described herein. In another aspect, tissue culture refers to the culture of protoplasts, calli, or plant cells, that are isolated from, or present in, intact parts of plants of one or more Powdery Mildew resistant pepper plant lines described herein, for example from the PBC167×SBY 99-1179 population.

Once Powdery Mildew resistant plants are produced, the plants themselves can be cultivated in accordance with conventional procedures. Powdery Mildew resistant progeny may be obtained through sexual reproduction. The seeds resulting from sexual reproduction can be recovered from the fruit of Powdery Mildew resistant plants and planted or otherwise grown as a means of propagation. Powdery Mildew resistant progeny may also be obtained from Powdery Mildew resistant plants through asexual reproduction. Protoplast or propagules (e.g., cuttings, scions or rootstocks) can be recovered from Powdery Mildew resistant plants or parts thereof and may be employed to propagate Powdery Mildew resistant plants.

The present invention also provides for and includes a container of pepper seeds in which pepper plants grown from greater than 50% of the seeds have resistance or partial resistance to Powdery Mildew. In another aspect, pepper plants grown from greater than 55%, 65%, 75%, 85%, 90%, 95%, 98%, or 99% of the pepper seeds in the container have Powdery Mildew resistance. Another aspect of the invention relates to seeds from a pepper plant selected from the group consisting of the PBC167×SBY 99-1179 population, and Powdery Mildew resistant progeny thereof, wherein pepper plants grown from about 50%, or greater than 50%, of the seeds have resistance or partial resistance to Powdery Mildew.

The container of pepper seeds can contain any number, weight or volume of seeds. For example, a container can contain about, or greater than about, 10, 25, 50, 200, 400, 700, 1000, 2000, 3000, or more seeds. In another aspect, a container can contain about, or greater than about, 1 gram, 5, 10, 15, 25, 100, 250, 500, or 1,000 grams of seeds. Alternatively, the container can contain about or at least, or greater than, about 1 ounce, 2, 4, 8, 10 ounces, 1 pound, 2, 4, 8, 12 pounds or more of seeds.

Containers of pepper seeds can be any container available in the art. For example, a container can be a box, a bag, a packet, a pouch, a tape roll, a foil, a pail, or a tube.

The present invention includes and provides for a container of pepper fruit from pepper plants having Powdery Mildew resistance. In one aspect, the container contains about 2, 5, 10, 20, 40, 80, 100, or more pepper fruit. In yet another aspect, the present invention provides a pepper branch having pepper fruit from a plant having resistance to Powdery Mildew.

One aspect of the invention relates to dried, or otherwise processed, pepper fruit, produced by a pepper plant having a genome that comprises at least one genetic locus giving rise to Powdery Mildew resistance when expressed in a pepper plant. Processed pepper fruit includes, but is not limited to fruit pulp, stewed peppers, canned, pickled, minced, sliced, ground, or crushed pepper fruit. In some aspects, the dried, pickled, or otherwise processed pepper fruit, is the fruit of a pepper plant of a line selected from the group consisting of the PBC167×SBY 99-1179 population.

The present invention provides for an inbred pepper plant having resistance to Powdery Mildew, wherein the resistance is exhibited when the plant is in contact with *Leveillula taurica*. In one aspect, the inbred pepper plant is derived from accession PBC167, available from the United States Department of Agriculture (USDA; Beltsville, Md., USA) germplasm collection under PI640507.

The present invention includes and provides for *Capsicum* plants having at least one allele linked to or conferring a Powdery Mildew resistance trait. The Powdery Mildew resistant pepper plants can be either heterozygous or homozygous for the Powdery Mildew resistance trait. In one embodiment, the Powdery Mildew resistant trait can be linked to variations in a single gene (e.g., linked to one or more alleles of a single gene). In another embodiment, the Powdery Mildew resistance trait can be linked to variations at one or one or more QTL. In a yet another embodiment, the Powdery Mildew resistant pepper plants are homozygous for the Powdery Mildew resistance trait.

The present invention provides progeny of pepper plants having resistance to Powdery Mildew. As used herein, progeny include not only, without limitation, the products of any cross (be it a backcross or otherwise) between two plants, but all progeny whose pedigree traces back to the original cross. In one aspect of the present invention, the progeny contain about 50%, 25%, 12.5% or less nuclear DNA from a Powdery Mildew resistant pepper plant and expresses the genetic material that provides Powdery Mildew resistance. Representative populations of pepper plants comprising progeny having resistance to Powdery Mildew include progeny of the cross of susceptible parent SBY 99-1179×resistant parent PBC167.

One embodiment of the present invention provides for a Powdery Mildew resistant pepper plant that contains a genetic marker linked to one or more Powdery Mildew resistance locus or loci. By "Powdery Mildew resistance locus" is meant a locus that contributes to Powdery Mildew resistance either alone or in combination with one or more other Powdery Mildew resistance locus or loci. By "contributes to Powdery Mildew resistance" it is meant that the degree of Powdery Mildew resistance is increased in the corresponding plant, either when the locus is alone or in combination with one or more other locus or loci.

In one embodiment of the invention, a marker linked to one or more Powdery Mildew resistance loci includes one or more of the following: NE0235653, NE0238847, NE0237736, NE0236986, NE0236080, NE0237755, NE0239177, NE0238603, NE0238046, NE0237823, NE0230886, NE0240044, NE0237442, NE0238362, NE0238536, NE0236808, NE0238448, NE0241383, NE0240496, NE0237841, NE0239164, NE0240741, NE0236790, NE0238624, NE0240275, NE0238899, NE0238734, NE0240256, NE0237985, NE0239638, NE0239147, NE0240589, NE0237975, NE0239291, NE0235654, NE0238449, NE0240786, NE0239990, NE0231151, NE0240438, NE0237121, NE0238426, NE0235272, NE0237901, NE0237351, NE0241057, NE0237348, NE0240958, NCANN005704058, NCANN005704056, NCANN005704052, and NCANN005704049, comprising a single nucleotide polymorphism of one of SEQ ID NOs:1-44.

As used herein, linkage of two nucleic acid sequences, including a nucleic acid marker sequence and a nucleic acid sequence of a genetic locus imparting a desired trait such as Powdery Mildew resistance, may be genetic or physical or both. In one aspect of the invention, the nucleic acid marker and genetic locus conferring Powdery Mildew resistance are genetically linked, and exhibit a LOD score of greater than 2.0, as judged by interval mapping for the Powdery Mildew resistance trait based on maximum likelihood methods described by Lander and Botstein, 1989 (Genetics, 121:185-199), and implemented in the software package MAPMAKER (e.g. Lander et al., *Genomics* 1:174-181, (1987); default parameters). Alternatively, other software such as QTL Cartographer v1.17 (Basten et al., Zmap-a QTL cartographer. In: Proceedings of the 5th World Congress on Genetics Applied to Livestock Production: Computing Strategies and Software, edited by C. Smith, J. S. Gavora, B. Benkel, J. Chesnais, W. Fairfull, J. P. Gibson, B. W. Kennedy and E. B. Burnside. Volume 22, pages 65-66. Organizing Committee, 5th World Congress on Genetics Applied to Livestock Production, Guelph, Ontario, Canada, 1994; and Basten et al., QTL Cartographer, Version 1.17. Department of Statistics, North Carolina State University, Raleigh, N.C., 2004) may be used. Mapping of QTL is well-described (e.g. WO 90/04651; U.S. Pat. Nos. 5,492,547, 5,981,832, 6,455,758; reviewed in Flint-Garcia et al. 2003 (*Ann. Rev. Plant Biol.* 54:357-374, the disclosures of which are hereby incorporated by reference). In other embodiments, the marker and region conferring Powdery Mildew resistance are genetically linked and exhibit a LOD score of greater than 3.0, or a LOD score of greater than 6.0, 9.0, 12.0, 15.0, or 18.0. In one embodiment, the marker and region contributing to Powdery Mildew resistance are genetically linked and exhibit a LOD score of between about 14 and about 20. When assigning the presence of a QTL, the LOD threshold score associated with a QTL analysis as described herein may be determined to be significant at the 95% confidence level, or higher, such as at the 98% or 99% confidence level.

In another aspect, the nucleic acid marker is genetically linked at a distance of between about 0 and about 50 cM to the Powdery Mildew resistance locus. In other embodiments, the distance between the nucleic acid marker and the Powdery Mildew resistance locus is between about 0 and about 35 cM, or between about 0 and about 25 cM, or between about 0 and about 15 cM, or between about 0 and about 10 cM, or between about 0 and about 5 cM, including less than about 4, 3, 2 or 1 cM.

In yet another aspect, the invention provides a pepper plant comprising an introgressed chromosomal region from chromosome 4 of PBC167 or a progeny plant thereof, of about 40 cM or less within the region defined as spanning the positions of SNP marker NE0235653 and SNP marker NE0240958; or SNP marker NE0235653 and SNP marker NE0237348.

In another aspect, the nucleic acid marker sequence may be physically linked to a Powdery Mildew resistance locus. In some aspects, the nucleic acid sequence of the genetic marker specifically hybridizes to a nucleic acid molecule having a sequence that is within about 100 Mbp, or about 80 Mbp, or about 75 Mbp, or about 70 Mbp, or about 65 Mbp of a Powdery Mildew resistance locus. In another aspect, the nucleic acid sequence of the genetic marker specifically hybridizes to a nucleic acid molecule having a sequence of any of SEQ ID NOs:1-44, or a complement thereof.

As used herein, two nucleic acid molecules are said to be capable of hybridizing to one another if the two molecules are capable of forming an anti-parallel, double-stranded nucleic acid structure. Conventional stringency conditions are described by Sambrook et al., Molecular Cloning, A Laboratory Manual, 2nd Ed., Cold Spring Harbor Press, Cold Spring Harbor, N.Y. (1989) and by Haymes et al., Nucleic Acid Hybridization, A Practical Approach, IRL Press, Washington, D.C. (1985). Departures from complete complementarity are therefore permissible, as long as such departures do not completely preclude the capacity of the molecules to form a double-stranded structure. Thus, in order for a nucleic acid molecule to serve as a primer or probe it need only be sufficiently complementary in sequence to be able to form a stable double-stranded structure under the particular solvent and salt concentrations employed.

Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in Current Protocols in Molecular Biology, John Wiley & Sons, N.Y. (1989), 6.3.1-6.3.6. In some embodiments, hybridization conditions can be high, moderate or low stringency conditions. Preferred conditions include those using 50% formamide, 5.0×SSC, 1% SDS and incubation at 42° C. for 14 hours, followed by a wash using 0.2×SSC, 1% SDS and incubation at 65° C.

The specificity of hybridization can be affected by post-hybridization washes. For example, the salt concentration in the wash step can be selected from a low stringency of about 2.0×SSC at 50° C. to a moderate stringency of about 1.0×SSC at 50° C. to a high stringency of about 0.2×SSC at 50° C. In addition, the temperature in the wash step can be increased from low stringency conditions at room temperature, about 22° C., to moderate stringency conditions at about 50° C., to high stringency conditions at about 65° C. Both temperature and salt concentration may be varied, or either the temperature or the salt concentration may be held constant while the other variable is changed. In some aspects, the wash step can be performed for 5, 10, 15, 20, 25, 30, or more minutes. In another aspect, the wash step is performed for about 20 minutes. In yet another aspect, the wash step can be repeated 1, 2, 3, 4, or more times using the selected salt concentration, temperature, and time. In another aspect, the wash step is repeated twice.

A genetic marker profile of a plant may be predictive of the agronomic traits of a hybrid produced using that inbred. For example, if an inbred plant of known genetic marker profile and phenotype is crossed with a second inbred of known genetic marker profile and phenotype it is possible to predict the phenotype of the F1 hybrid based on the combined genetic marker profiles of the parent inbreds. Methods for prediction of hybrid performance from genetic marker data are disclosed in U.S. Pat. No. 5,492,547, the disclosure of which is specifically incorporated herein by reference in its entirety. Such predictions may be made using any suitable genetic marker, for example, SSRs, INDELs, RFLPs, AFLPs, SNPs, ISSRs, or isozymes.

Additional markers, such as SSRs, AFLP markers, RFLP markers, RAPD markers, phenotypic markers, SNPs, isozyme markers, or microarray transcription profiles that are genetically linked to or correlated with Powdery Mildew resistance can be utilized (Walton, Seed World 22-29 (July, 1993); Burow and Blake, Molecular Dissection of Complex Traits, 13-29, Eds. Paterson, CRC Press, New York (1988)). Methods to isolate such markers and to design probes or primers useful in following the presence of such markers are known in the art. For example, locus-specific SSRs can be obtained by screening a pepper genomic library for SSRs, sequencing of "positive" clones, designing primers which flank the repeats, and amplifying genomic DNA with these primers. Likewise, SNP markers may be identified as well.

The genetic linkage of marker molecules to Powdery Mildew resistance can be established by a gene mapping model such as, without limitation, the flanking marker model, and interval mapping, based on maximum likelihood methods described by Lander and Botstein, 1989 (Genetics, 121:185-199), and implemented in the software packages MAPMAKER (Whitehead Institute for Biomedical Research, Cambridge Mass., USA) or QTL Cartographer (North Carolina State University, Bioinformatics Research Center) or the like. A maximum likelihood estimate (MLE) for the presence of a marker is calculated, together with an MLE assuming no trait effect, to avoid false positives. A log 10 of an odds ratio (LOD) is then calculated as: LOD=log 10 (MLE for the presence of a trait (MLE given no linked trait)).

The LOD score essentially indicates how much more likely the data are to have arisen assuming the presence of a resistance allele rather than in its absence. The LOD threshold value for avoiding a false positive with a given confidence, say 95%, depends on the number of markers and the length of the genome. Graphs indicating LOD thresholds are set forth in Lander and Botstein (1989), and further described by Ars and Moreno-Gonzalez, Plant Breeding, Hayward, Bosemark, Romagosa (eds.) Chapman & Hall, London, pp. 314-331 (1993), and van Ooijen (Heredity 83:613-624, 1999).

Selection of appropriate mapping or segregation populations is important in trait mapping. The choice of appropriate mapping population depends on the type of marker systems employed (Tanksley et al., Molecular mapping plant chromosomes. Chromosome structure and function: Impact of new concepts J. P. Gustafson and R. Appels (eds.), Plenum Press, New York, pp. 157-173 (1988)). Consideration must be given to the source of parents (adapted vs. exotic) used in the mapping population. Chromosome pairing and recombination rates can be severely disturbed (suppressed) in wide crosses (adapted×exotic) and generally yield greatly reduced linkage distances. Wide crosses will usually provide segregating populations with a relatively large array of polymorphisms when compared to progeny in a narrow cross (adapted×adapted).

Advanced breeding lines are collected from breeding programs. These are tested for their phenotype (e.g. their disease score reactions to Powdery Mildew infection), and genotyped for markers in the Powdery Mildew QTL intervals. From these data, the smallest genetic interval is identified within each QTL containing the donor parent (DP) favorable allele among the Powdery Mildew resistant lines. This interval is inferred to be critical for conferring resistance to Powdery Mildew. Candidate genetic intervals associated with Powdery Mildew resistance were detected as regions showing enhanced frequency of the favorable allele from the Powdery Mildew resistance donor PBC167 relative to a baseline set of Powdery Mildew susceptible samples from the same germplasm classification type (GCT). For example, comparisons may be made among Powdery Mildew resistant and susceptible inbreds within a single GCT and a single breeding program. Allele frequency shifts between phenotypic classes may be detected by calculating a linkage assessment score (LAS) as: LAS=(Frequency of favorable allele in samples with favorable phenotype)× (Frequency of unfavorable allele in samples with unfavorable phenotype).

As used herein, the progeny include not only, without limitation, the products of any cross (be it a backcross or otherwise) between two plants, but all progeny whose pedigree traces back to the original cross. Specifically, without limitation, such progeny include plants that have 50%, 25%, 12.5% or less nuclear DNA derived from one of the two originally crossed plants. As used herein, a second plant is derived from a first plant if the second plant's pedigree includes the first plant.

The present invention provides a genetic complement of the pepper lines described herein. Further provided is a hybrid genetic complement, wherein the complement is formed by the combination of a haploid genetic complement from elite inbred pepper lines described herein and another haploid genetic complement. Means for determining such a genetic complement are well-known in the art.

As used herein, the phrase "genetic complement" means an aggregate of nucleotide sequences, the expression of which defines the phenotype of a plant, such as a pepper plant of the genus Capsicum or a cell or tissue of that plant. By way of example, a pepper plant of the genus Capsicum is genotyped to determine a representative sample of the inherited markers it possesses. Markers are preferably inherited in codominant fashion so that the presence of both alleles at a diploid locus are readily detectable, and they are free of environmental variation, i.e., their heritability is close to, or equal to, 1. This genotyping is preferably performed on at least one generation of the descendant plant for which the numerical value of the trait or traits of interest are also determined. The array of single locus genotypes is expressed as a profile of marker alleles, two at each locus for a diploid plant. The marker allelic composition of each locus can be either homozygous or heterozygous. Homozygosity is a condition where both alleles at a locus are characterized by the same conditions of the genome at a locus (e.g., the same nucleotide sequence). Heterozygosity refers to different conditions of the genome at a locus. Potentially any type of genetic marker could be used, for example, simple sequence repeats (SSRs), insertion/deletion polymorphism (INDEL), restriction fragment length polymorphisms (RFLPs), amplified fragment length polymorphisms (AFLPs), single nucleotide polymorphisms (SNPs), and isozymes.

Considerable genetic information can be obtained from a completely classified F2 population using a codominant marker system (Mather, Measurement of Linkage in Heredity: Methuen and Co., (1938)). An F2 population is the first generation of self or sib pollination after the hybrid seed is produced. Usually a single F1 plant is self or sib pollinated to generate a population segregating for the nuclear-encoded genes in a Mendelian (1:2:1) fashion.

In contrast to the use of codominant markers, using dominant markers often requires progeny tests (e.g., F3 or back cross self families) to identify heterozygous individuals. The information gathered can be equivalent to that obtained in a completely classified F2 population. This procedure is, however, often prohibitive because of the cost and time involved in progeny testing. Progeny testing of F2 individuals is often used in map construction where error is associated with single plant phenotyping, or when sampling the plants for genotyping affects the ability to perform accurate phenotyping, or where trait expression is controlled by a QTL. Segregation data from progeny test populations (e.g., F3 or backcrossed or selfed families) can be used in trait mapping. Marker-assisted selection can then be applied to subsequent progeny based on marker-trait map associations (F2, F3), where linkage has not been completely disassociated by recombination events (i.e., maximum disequilibrium).

Recombinant inbred lines (RILs) (genetically related lines; usually >F5) can be used as a mapping population. RILs can be developed by selfing F2 plants, then selfing the resultant F3 plants, and repeating this generational selfing process, thereby increasing homozygosity. Information obtained from dominant markers can be maximized by using RILs because all loci are homozygous or nearly so. Under conditions of tight linkage (i.e., about <10% recombination), dominant and co-dominant markers evaluated in RIL populations provide more information per individual than either marker type in backcross populations (e.g. Reiter et al., 1992; *Proc. Natl. Acad. Sci.* (U.S.A.) 89:1477-1481). However, as the distance between markers becomes larger (i.e., loci become more independent), the information in RIL populations decreases dramatically when compared to codominant markers.

Backcross populations can be utilized as mapping populations. A backcross population (BC) can be created by crossing an F1 to one of its parents. Typically, backcross populations are created to recover the desirable traits (which may include most of the genes) from a recurrent parental line (the parent that is employed in the backcrosses) while adding one or a few traits from the second parental line, which is often referred to as the donor. A series of backcrosses to the recurrent parent can be made to recover most of the recurrent parent's desirable traits. Thus a population is created consisting of individuals nearly like the recurrent parent, wherein each individual carries varying amounts or a mosaic of genomic regions from the donor parent. Backcross populations can be useful for mapping dominant markers particularly if all loci in the recurrent parent are homozygous and the donor and recurrent parent have contrasting polymorphic marker alleles (Reiter et al., 1992; Proc. Natl. Acad. Sci. (U.S.A.) 89:1477-1481).

Information obtained from backcross populations using either codominant or dominant markers is less than that obtained from completely classified F2 populations because recombination events involving one, rather than two, gametes are sampled per plant. Backcross populations, however, are more informative (at low marker saturation) when compared to RILs as the distance between linked loci increases in RIL populations (i.e., about 15% recombination). Increased recombination can be beneficial for resolution of tight linkages, but may be undesirable in the construction of maps with low marker saturation.

Near-isogenic lines (NIL) created by many backcrosses to produce an array of individuals that are nearly identical in genetic composition except for the trait or genomic region under interrogation can be used as a mapping population. In mapping with NILs, only a portion of the loci polymorphic between the parental lines are expected to segregate in the highly homozygous NIL population. Those loci that are polymorphic in a NIL population, however, are likely to be linked to the trait of interest.

Bulk segregant analysis (BSA) is a method developed for the rapid identification of linkage between markers and traits of interest (Michelmore, et al., 1991; *Proc. Natl. Acad. Sci.* (U.S.A.) 88:9828-9832). In BSA, two bulk DNA samples are drawn from a segregating population originating from a single cross. These bulk samples contain individuals that are identical for a particular trait (e.g., resistant or susceptible to a particular pathogen) or genomic region but arbitrary at unlinked regions (i.e., heterozygous). Regions unlinked to the target trait will not differ between the bulked samples of many individuals in BSA.

In another aspect, the present invention provides a method of producing a Powdery Mildew resistant pepper plant comprising: (a) crossing a pepper line having Powdery Mildew resistance with a second pepper line lacking Powdery Mildew resistance to form a segregating population; (b) screening the population for resistance to Powdery Mildew; and (c) selecting one or more members of the population having said Powdery Mildew resistance. In one aspect, the pepper line having Powdery Mildew resistance is crossed with the second pepper line for at least two generations (e.g., creating either an F2 or BC1S1 population). In a particular embodiment, the pepper line having Powdery Mildew resistance is PBC167, or a progeny thereof. In another aspect, plants are identified as Powdery Mildew resistant prior to crossing. In one aspect, plants can be selected on the basis of partial or complete resistance to Powdery Mildew. In one aspect, the segregating population is self-crossed and the subsequent population is screened for resistance.

In another aspect, the present invention provides a method of introgressing Powdery Mildew resistance into a pepper plant comprising: (a) crossing at least a first pepper line having Powdery Mildew resistance with a second pepper line to form a segregating population; (b) screening said population for resistance to Powdery Mildew; and (c) selecting at least one member of said population exhibiting Powdery Mildew resistance. In one aspect, the pepper line having Powdery Mildew resistance is crossed with the second pepper line for at least two generations (e.g., creating either an F2 or BC1S1 population), or up to 2-10 generations. In another aspect, plants are identified as Powdery Mildew resistant prior to crossing. In one aspect, the segregating population is self-crossed and the subsequent population is screened for resistance.

Pepper plants (and parts thereof, including seed, pollen, and ovules) generated using a method of the present invention are also provided, and can be part of or generated from a breeding program. The choice of breeding method depends on the mode of plant reproduction, the heritability of the trait(s) being improved, and the type of cultivar used commercially (e.g., F1 hybrid cultivar, pure line cultivar, etc). Selected, non-limiting approaches for breeding the plants of the present invention are set forth below. A breeding program can be enhanced using marker assisted selection of the progeny of any cross. It is further understood that any commercial and non-commercial cultivars can be utilized in a breeding program. Factors such as, for example, emergence vigor, vegetative vigor, stress tolerance, disease resistance, branching, flowering, fruit size, fruit quality, and/or fruit yield will generally dictate the choice.

For highly heritable traits, a choice of superior individual plants evaluated at a single location will be effective, whereas for traits with low heritability, selection should be based on statistical analyses (e.g., mean values) obtained from replicated evaluations of families of related plants. Popular selection methods commonly include pedigree selection, modified pedigree selection, mass selection, and recurrent selection. In a preferred embodiment a backcross or recurrent breeding program is undertaken.

The complexity of inheritance influences choice of the breeding method. Backcross breeding can be used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Breeding lines can be tested and compared to appropriate standards in environments representative of the commercial target area(s) for two or more generations. The best lines are candidates as parents for new commercial cultivars; those still deficient in traits may be used as parents for hybrids, or to produce new populations for further selection.

One method of identifying a superior plant is to observe its performance relative to other experimental plants and to a widely grown standard cultivar. If a single observation is inconclusive, replicated observations can provide a better estimate of its genetic worth. A breeder can select and cross two or more parental lines, followed by repeated self or sibling pollination and selection, producing many new genetic combinations.

The development of new pepper lines requires the development and selection of pepper varieties, the crossing of these varieties and selection of superior hybrid crosses. The hybrid seed can be produced by manual crosses between selected male-fertile parents or by using male sterility systems. Hybrids can be selected for certain single gene traits such as flower color, seed yield or herbicide resistance that indicate that the seed is truly a hybrid. Additional data on parental lines, as well as the phenotype of the hybrid, influence the breeder's decision whether to continue with the specific hybrid cross.

Pedigree breeding and recurrent selection breeding methods can be used to develop cultivars from breeding populations. Breeding programs combine desirable traits from two or more cultivars or various broad-based sources into breeding pools from which cultivars are developed by selfing and selection of desired phenotypes into parent lines. These lines are used to produce new cultivars. New cultivars can be evaluated to determine which have commercial potential.

Pedigree breeding is used commonly for the improvement of self-pollinating crops. Two parents who possess favorable, complementary traits are crossed to produce an F1. An F2 population is produced by selfing one or several F1's. Selection of the best individuals in the best families is performed. Replicated testing of families can begin in the F4 generation to improve the effectiveness of selection for traits with low heritability. At an advanced stage of inbreeding (i.e., F6 and F7), the best lines or mixtures of phenotypically similar lines are tested for potential release as new cultivars.

Backcross breeding and cross breeding have been used to transfer genes for a simply inherited, highly heritable trait into a desirable homozygous cultivar or inbred line, which is the recurrent parent. The source of the trait to be transferred is called the donor parent. The resulting plant obtained from a successful backcrossing program is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. After multiple backcrossing generations with selection, the resulting line is expected to have the attributes of the recurrent parent (e.g., cultivar) and the desirable trait transferred from the donor parent.

Cross breeding or backcross breeding of a Powdery Mildew resistant pepper plant may be conducted where the other parent (second pepper plant) is Powdery Mildew resistant or the other parent is not Powdery Mildew resistant.

Pepper plants generated of the invention may be generated using a single-seed descent procedure. The single-seed descent procedure, in the strict sense, refers to planting a segregating population, then selecting one plant in this and each subsequent generation to self and create the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

Descriptions of other breeding methods that are commonly used for different traits and crops can be found in one of several available reference books (e.g., Fehr, Principles of Cultivar Development Vol. 1, pp. 2-3 (1987)).

In one aspect of the present invention, the source of the Powdery Mildew resistance trait for use in a breeding program is derived from a plant selected from the group consisting of PBC167 and progeny pepper plants of pepper line PBC167, such as members of the PBC167×SBY 99-1179 mapping population disclosed herein. In another aspect, the source of the Powdery Mildew resistance trait for use in a breeding program is not derived from a plant selected from the group consisting of PBC167 and progeny pepper plants of pepper line PBC167, such as members of the PBC167×SBY 99-1179 mapping population disclosed herein. Also included in the invention is a pepper plant having a genome, wherein said genome comprises a genetic locus conferring resistance to Powdery Mildew, wherein said genetic locus contains one or more genetic markers linked to said genetic locus conferring resistance to Powdery Mildew, and wherein said pepper plant is not accession PBC167.

In another aspect, additional sources of Powdery Mildew resistance for use in a breeding program can be identified by screening pepper germplasm for resistance to Powdery Mildew. In yet another aspect, pepper plants can be screened for Powdery Mildew resistance by identifying germplasm exhibiting reduced disease symptoms relative to a control pepper plant after inoculation or infection. In one aspect, pepper plants can be screened for resistance to Powdery Mildew using a test such as a field or greenhouse screen and disease rating schemes as described in Example 4.

In another aspect, additional sources of Powdery Mildew resistance for use in a breeding program can be identified by screening with one or more molecular markers linked to a genetic locus conferring resistance to Powdery Mildew, such as those identified herein.

In another aspect, additional sources of Powdery Mildew resistance for use in a breeding program can be identified by a combination of screening pepper plants for reduced disease symptoms and screening with one or more molecular markers linked to a genetic locus contributing to resistance to Powdery Mildew.

In another aspect, pepper lines having Powdery Mildew resistance can be used in breeding programs to combine Powdery Mildew resistance with additional traits of interest. In one aspect, Powdery Mildew resistance can be combined with any additional trait, including disease resistant traits, yield traits, and fruit quality traits. For example, breeding programs can be used to combine the Powdery Mildew resistance trait with alleles that contribute to size and shape in pepper fruit. Breeding programs can also be used to combine Powdery Mildew resistance with one or more disease resistant traits. Other disease traits include resistance to biotic diseases caused by viroids, virus, bacteria, fungi, nematodes, and insects. Such disease resistant traits include, without limitation, resistance to: Alfalfa mosaic virus, Anthracnose, Bacterial Canker, Bacterial Spot, Bacterial stem and peduncle canker, Bacterial Wilt, Beet curly top virus, *Cercospora* Leaf Spot, *Chaenophora* Blight, Cucumber mosaic virus, Fungal root rots (*Fusarium* Wilt, *Verticillium* Wilt, Damping-off and root rot, *Phytophthora* Blight), Geminiviruses (Pepper golden mosaic virus, Pepper huasteco virus, Sinaloa tomato leaf curl), Gray Leaf Spot, Gray Mold, Peanut bud necrosis virus, Potato X virus, Potyviruses (Potato virus Y, Pepper mottle virus, Tobacco etch virus, Pepper yellow mosaic virus, Chilli veinal mottle virus), Powdery Mildew, Root-knot nematode, Southern Blight/*Sclerotium* Wilt, *Syringae* seedling blight and leaf spot, Tobamoviruses (Tomato mosaic virus, Tobacco mosaic virus, Pepper mild mottle virus), Tospoviruses (Tomato spotted wilt virus) and White Mold (pink rot, watery soft rot). Additional traits may also include resistance to abiotic disorders such as those caused by extremes in nutritional and environmental conditions or other physiological disorders (e.g. Blossom-end rot). In another aspect, the traits that are combined can be coinherited in subsequent crosses.

The present invention also provides for parts of the Powdery Mildew resistant pepper plants produced by a method of the present invention. Parts of pepper plants, without limitation, include plant cells or parts of plant cells, seed, endosperm, meristem, flower, anther, ovule, pollen, fruit, flowers, stems, roots, stalks or leaves, scions, and root stocks. Plant parts also include the parts of a pepper fruit, which include the placenta, columella and pericarp. In one embodiment of the present invention, the plant part is a seed.

The invention further provides for parts of a pepper plant having a genome, that comprises at least one genetic locus giving rise to Powdery Mildew resistance in the pepper plant. One aspect of the invention provides a Powdery Mildew pepper plant, or the fruit or seeds thereof, wherein the pepper plant, or the fruit thereof, expresses one, or two, or three, or more independently selected desirable traits in addition to Powdery Mildew resistance. In one embodiment, the "desirable trait" or "desirable traits" are selected from the group consisting of: fruit size, shape, color, surface appearance; seed number, seed size, locule number; pericarp thickness and toughness; taste and shelf life, plant vigor, leaf shape, leaf length, leaf color, plant height, whether the plant is determinate or not, time to maturity, adaptation to field growth, adaptation to greenhouse growth, and resistance to one or more diseases, disease causing organisms or physiological disorders such as Alfalfa mosaic virus, Anthracnose, Bacterial Canker, Bacterial Spot, Bacterial stem and peduncle canker, Bacterial Wilt, Beet curly top virus, Blossom-end rot, *Cercospora* Leaf Spot, Chilli veinal mottle virus, *Chaenophora* Blight, Cucumber mosaic virus, Damping-off and root rot, Fungal root rots, *Fusarium* Wilt, Geminiviruses, Gray Leaf Spot, Gray Mold, Peanut bud necrosis virus, Pepper golden mosaic virus, Pepper huasteco virus, Pepper mild mottle virus, Pepper mottle virus, Pepper yellow mosaic virus, *Phytophthora* Blight, Potato X virus, Potato Y virus, Powdery Mildew, Root-knot nematode, Sinaloa tomato leaf curl, Southern Blight/*Sclerotium* wilt, *Syringae* seedling blight and leaf spot, Tobacco etch virus, Tobacco mosaic virus, Tobamoviruses, Tomato mosaic virus, Tomato spotted wilt virus, Tospoviruses, *Verticillium* Wilt and White Mold (pink rot, watery soft rot). In another embodiment the "desirable trait" or "desirable traits" are selected from the group consisting of: fruit size, fruit shape, fruit color, fruit quality acceptable to market, and the shelf life of fruit.

In other aspects of the invention, the plants bearing one or more desirable traits in addition to Powdery Mildew resistance display a greater than 10%, or a greater than 30%, or a greater than 60%, or a greater than 80% reduction in *Leveillula taurica* sporulation relative to a non-resistant control plant upon inoculation or infection with Powdery Mildew. Another aspect of the present invention is directed to a method of producing a Powdery Mildew resistant pepper plant comprising: crossing a pepper line having Powdery Mildew resistance with a second plant lacking Powdery Mildew resistance but capable of donating one or more of the aforementioned desirable traits.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Identification of Resistance to Pepper Powdery Mildew Caused by *Leveillula taurica*

To identify germplasm exhibiting resistance to Powdery Mildew caused by the fungus *Leveillula taurica*, a screen was undertaken with germplasm under disease pressure conditions. A line derived from PBC167 was identified in this screen as a source of resistance to *Leveillula taurica*. PBC167 is available from the United States Department of Agriculture (USDA) germplasm collection under PI640507. In order to develop tools with which to track this PBC167-derived *Leveillula taurica* resistance, an association mapping analysis was undertaken.

Example 2: Development of a Mapping Population

A population was developed to create linkage and QTL maps. The pepper line PBC167 displays resistance to *Leveillula taurica*. Pepper line SBY 99-1179 is susceptible to Powdery Mildew caused by the fungus *Leveillula taurica*. In SBY 99-1179, introgression of PBC167-derived sequence effects the resistance response. Plants derived from crosses between these pepper lines with distinct levels of *Leveillula* taurica resistance were obtained, and certain resulting lines were genotyped and phenotyped for association mapping analysis.

Example 3: Identification of *Leveillula taurica* Resistance Mapping Population Genotypes The BC1 generation (n=87) of the mapping population from Example 2 was genotyped at a selection of SNP markers collectively spanning each chromosome in the plant genome.

Example 4: Mapping Population *Leveillula taurica* Disease-Response Phenotyping

Corresponding progenies (BC1F2; n=96) of the population genotyped in Example 3 were evaluated for *Leveillula taurica* resistance under greenhouse bioassay conditions. In the greenhouse in Woodland, Calif., plants were inoculated at the 3-4 true leaf stage, approximately 20 days post seedling. Plants were organized in a randomized block design. Using a spray bottle with $1\times10^4$ c/mL of conidia in reverse osmosis purified water, plants were sprayed uniformly on the foliage of all plants until runoff. Prior to inoculum preparation, a locally collected *Leveillula taurica* strain was maintained on the susceptible host Yolo Wonder B. After allowing infection to develop, plants were scored on a three point scale of 1 (resistant) to 9 (susceptible).

The following rating scale definitions were used to characterize the greenhouse trial:

a. 1 (Resistant): No sporulation b. 5 (Intermediate Resistance): Very light sporulation usually underneath the leaf c. 9 (Susceptible): White sporulation on the whole surface of inoculated leaves The same BC1F2 families were also evaluated under field conditions where progenies (n=100) were evaluated for Powdery Mildew resistance in a field in Woodland, Calif. after allowing disease pressure to develop naturally. The trial was set in a randomized block design with 3 replications. Each plot consisted of >10 plants. All plants in each plot were scored on a three point scale of 1 (resistant) to 9 (susceptible).

The following rating scale definitions were used to characterize the field trial:

d. 1 (Resistant): No sporulation e. 5 (Intermediate Resistance): Very light sporulation usually underneath the leaf f. 9 (Susceptible): White sporulation on the whole surface of inoculated leaves Progenies (n=96) were additionally evaluated for Powdery Mildew resistance in greenhouse and field conditions in Almeria, Spain with isolates from that region. For greenhouse bioassay evaluation, pepper plants were grown in rock wool and distributed on a table with a layer of soil, leaving around 7-8 cm between rock wools. The soil was watered daily, without splashing the pepper plants. The humid layer of soil helps to obtain the necessary relative humidity (RH) for the assay. Inoculation was carried out at the growth stage of 4 fully grown leaves by spraying a conidia suspension as described: Inoculum of the fungus was collected from an infected greenhouse by picking leaves with abundant white powdery mildew sporulation. Conidia were obtained from leaves on the day of inoculation by washing the symptomatic leaves with the aid of a fine brush, followed immediately by dilution to 4×104 conidia/ml with a Bürker Türk haemocytometer. The conidia suspension was filtered through cheesecloth to remove plant material. For the inoculation, the lower side of the leaves was sprayed with conidia suspension. Inoculations were performed in the late afternoon, avoiding peak temperatures, and a high soil moisture status was maintained. After inoculation, plants were allowed to develop symptom expression in a temperature/humidity-controlled greenhouse environment (Night 18° C.-Day 22° C. and 65%-80% HR). Evaluation of symptoms was assessed based on sporulation density and number of spots per leaf at 25-30 days post inoculation (dpi) according to a scale from 0 to 5 as follows:

| Density of sporulation: | Spot per leaf: |
|---|---|
| 0 = no visible sporulation | 0 = No spots |
| 1 = few spores per spot, <10% | 1 = 1 or 2 spots |
| 2 = light sporulation, 25% | 2 = 3, 4 or 5 spots |
| 3 = strong sporulation, easy to see 25-50% | 3 = more than 5 spots per leaf |
| 4 = very strong sporulation 50-75% | 4 = 50% of leaf affected |
| 5 = sporulation on upper and lower side of leaf | 5 = 90% of leaf affected |

Example 5: QTL Mapping

Single Marker Regression:

The R/qtl function scanone (method=mr) was used to scan for single QTL across the whole genome. Genome wide 1000 permutations were generated and a 5% false discovery rate was utilized as a significance threshold. One QTL on Chromosome 4 was detected with this threshold. Two QTL markers were identified by this methodology as being significantly linked to the QTL (Table 2).

TABLE 2

QTL Linked Markers identified by Marker Regression.

| | LOD | | | | |
|---|---|---|---|---|---|
| Marker | Wld_GH | Wld_Fld | Spain_GH | Spain_Fld | Chr |
| Threshold 5% | 3.12 | 3.49 | 3.18 | 3.2 | |
| NE0236790 | 51.9 | 13.7 | 38.1 | 19.1 | 4 |
| NE0237985 | 49.4 | 13.7 | 32.1 | 18.6 | 4 |

Where Wld = Woodland, California; Spain = Almeria, Spain; GH = greenhouse; and Fld = field.

Interval Mapping:

A non-parametric mapping model was adopted for QTL identification. Interval mapping using this non-parametric model was performed for adjusted phenotypic data at 1 cM intervals. LOD score significance was based on the 5% alpha threshold obtained with 1,000 permutations genome-wide.

A QTL was identified by all four sets of phenotypic data at almost the same location on chromosome 4 (Table 3 and FIGS. 1-2). Effects of markers associated with the QTL 2-LOD interval region are listed in Table 4.

TABLE 3

QTL identified by interval mapping.

| Phenotype | Threshold (5% FDR) | 1-LOD (cM) | 2-LOD (cM) | 3-LOD (cM) | Max LOD | Max LOD Position (cM) | Left MRN | Right MRN |
|---|---|---|---|---|---|---|---|---|
| Wld_GH | 2.88 | 14.1-32.7 | 11.7-39.7 | 7.7-40.7 | 13.4 | 23.7 | NE0236790 | NE0237985 |
| Wld_Fld | 2.75 | 16.7-26.7 | 11.7-37.6 | 7.7-42.7 | 7.17 | 23.7 | NE0236790 | NE0237985 |
| Spain_GH | 2.87 | 17.7-26.7 | 15.7-38.7 | 14.1-40.7 | 13.6 | 21.6 | NE0236808 | NE0237985 |
| Spain_Fld | 2.82 | 15.7-26.7 | 12.7-39.7 | 11.7-41.7 | 12.1 | 23.7 | NE0236790 | NE0237985 |

Where FDR = false discovery rate; and
MRN = marker number.

TABLE 4

Effects of Markers within QTL 2-LOD Interval Region.

| MRN | Chr | Position (cM) | Wld_GH | Wld_Fld | Spain_GH | Spain_Fld |
|---|---|---|---|---|---|---|
| NE0237823 | 4 | 11.6 | −3.6 | −3.3 | −2.3 | −1.7 |
| NE0237442 | 4 | 13.4 | −3.8 | −3.4 | −2.6 | −1.9 |
| NE0236808 | 4 | 14.1 | −3.8 | −3.4 | −2.6 | −1.9 |
| NE0238624 | 4 | 21.6 | −4.1 | −3.9 | −2.8 | −2.0 |
| NE0236790 | 4 | 21.6 | −4.1 | −3.9 | −2.8 | −2.0 |
| NE0237985 | 4 | 25.2 | −4.1 | −3.9 | −2.8 | −2.0 |
| NE0239147 | 4 | 26.8 | −4.0 | −3.6 | −2.7 | −1.9 |
| NE0240438 | 4 | 37.6 | −3.9 | −3.4 | −2.6 | −1.9 |
| NE0237348 | 4 | 45.3 | −2.8 | −2.6 | −2.0 | −1.4 |

Example 7: Segregation Ratio Confirms QTL Mapping Results

When looking at resistant vs. susceptible, the segregation ratio fits with a one dominant gene model (Table 5). This supports the single locus dominant inheritance and large QTL effect of Powdery Mildew resistance derived from PBC167 based on F2 and BC1 data (Table 5).

TABLE 5

Chi-square test of Fit for Single Dominant gene model of Powdery Mildew resistance in PBC167 derived BC1F2, after combining homozygous and heterozygous resistant plants into one group.

| BC1F2 | Observed | Expected |
|---|---|---|
| R (3/8) | 37 | 36 |
| S (5/8) | 59 | 60 |
| total | 96 | 96 |
| $X^2$ | | 0.044444 |
| p-value | | >0.50 |

TABLE 6

Chi-square analysis of Fit for Single Dominant gene model of Powdery Mildew resistance in PBC167.

| | Total plants | expected S | expected R | observed S | observed R | Chi-square | p-value | |
|---|---|---|---|---|---|---|---|---|
| F2 | 246 | 61.5 | 184.5 | 48 | 198 | 3.951 | 0.0468 | F2 (3:1) |
| BC1 | 244 | 122 | 122 | 134 | 110 | 2.361 | 0.1244 | BC1F1 (1:1) |

Example 8: Alignment of Mapped QTL Region to Pepper Consensus Map Allows Identification of Additional Markers Linked to the Region Conferring Resistance to Pepper Powdery Mildew Caused by *Leveillula taurica*

Markers associated with Powdery Mildew resistance and used for QTL mapping can be additionally placed on a pepper consensus map to locate additional markers associated with the QTL region on Chromosome 4 that confers resistance to pepper Powdery Mildew caused by *Leveillula taurica*. On pepper chromosome 4, approximate map position relative to other markers, in cM, is given where position 0 is the most distal marker known at the beginning of the chromosome (Table 7).

TABLE 7

Exemplary additional markers linked to QTL.

| MRN | Chromosome | Position (cM) |
|---|---|---|
| NE0235653 | 4 | 7.131 |
| NE0238847 | 4 | 8.152 |
| NE0237736 | 4 | 8.631 |
| NE0236986 | 4 | 9.093 |
| NE0236080 | 4 | 9.158 |
| NE0237755 | 4 | 10.125 |
| NE0239177 | 4 | 10.125 |
| NE0238603 | 4 | 10.893 |
| NE0238046 | 4 | 11.063 |
| NE0237823 | 4 | 11.565 |
| NE0230886 | 4 | 12.049 |
| NE0240044 | 4 | 12.049 |
| NE0237442 | 4 | 13.390 |
| NE0238362 | 4 | 13.416 |
| NE0238536 | 4 | 13.910 |
| NE0236808 | 4 | 14.110 |
| NE0238448 | 4 | 14.110 |
| NE0241383 | 4 | 14.110 |
| NE0240496 | 4 | 14.788 |
| NE0237841 | 4 | 16.764 |
| NE0239164 | 4 | 18.190 |
| NE0240741 | 4 | 18.611 |

TABLE 7-continued

Exemplary additional markers linked to QTL.

| MRN | Chromosome | Position (cM) |
|---|---|---|
| NE0236790 | 4 | 21.562 |
| NE0238624 | 4 | 21.562 |
| NE0240275 | 4 | 21.562 |
| NE0238899 | 4 | 24.871 |
| NE0238734 | 4 | 24.872 |
| NE0240256 | 4 | 25.108 |
| NE0237985 | 4 | 25.173 |
| NE0239638 | 4 | 25.885 |
| NE0239147 | 4 | 26.810 |
| NE0240589 | 4 | 29.496 |
| NE0237975 | 4 | 30.808 |
| NE0239291 | 4 | 31.511 |
| NE0235654 | 4 | 31.598 |
| NE0238449 | 4 | 34.387 |
| NE0240786 | 4 | 34.387 |
| NE0239990 | 4 | 34.844 |
| NE0231151 | 4 | 37.409 |
| NE0240438 | 4 | 37.571 |
| NE0237121 | 4 | 38.234 |
| NE0238426 | 4 | 38.412 |
| NE0235272 | 4 | 39.789 |
| NE0237901 | 4 | 39.882 |
| NE0237351 | 4 | 40.289 |
| NE0241057 | 4 | 42.610 |
| NE0237348 | 4 | 45.269 |
| NE0240958 | 4 | 45.269 |

Example 9: PBC167-Specific Marker Development

In order to obtain markers that were highly specific to PBC167, genomic DNA from PBC167 and a panel of susceptible inbred lines was resequenced. Several loci were identified that were monomorphic in the original PBC167 mapping population. Four of these loci yielded SNPs that were highly specific to PBC167 in a larger accuracy panel of 100+ inbreds (Table 8). The original four loci (NE0239291, NE0240589, NE0239638, NE0240275) were given derived-marker numbers to reflect the new SNPs from those amplicons. These new SNPs are highly-predictive of PBC167.

TABLE 8

PBC167-specific SNPs on chromosome 4.

| MRN | Derived-MRN | Position (cM) | PBC167 | Heterozygote | Parent |
|---|---|---|---|---|---|
| NE0239291 | NCANN005704049 | 31.51094 | TT | CT | CC |
| NE0240589 | NCANN005704052 | 29.49618 | CC | AC | AA |
| NE0239638 | NCANN005704056 | 25.88461 | CC | CT | TT |
| NE0240275 | NCANN005704058 | 21.56184 | GG | AG | AA |

All publications and patent applications cited herein are incorporated by reference to the same extent as if each individual publication or patent application was specifically and individually indicated to be incorporated by reference.

Although certain embodiments have been described in detail above, those having ordinary skill in the art will clearly understand that many modifications are possible in the embodiments without departing from the teachings thereof. All such modifications are intended to be encompassed within the invention as disclosed.

What is claimed is:

1. A method of producing an agronomically elite pepper plant of the genus *Capsicum* that displays improved resistance to Powdery Mildew, the method comprising introgressing into said plant at least a first chromosomal interval that confers the improved resistance to Powdery Mildew, wherein the chromosomal interval maps to a position between the sequence represented by marker NE0240275 and marker NE0240958, or the chromosomal interval maps to a position between the sequence represented by marker NE0240275 and marker NE0237348, which each map to approximately 21.56 cM and 45.27 cM, respectively, on the genetic map of the linkage group termed pepper chromosome 4, and wherein the chromosomal interval comprises at least a first marker indicative of the presence of said resistance to Powdery Mildew selected from the group consisting of marker NE0239291, marker NE0240589, marker NE0239147, marker NE0239638, marker NCANN005704056, marker NE0237985, marker NE0240256, marker NE0238899, marker NE0238734, marker NE0236790, and marker NE0240275.

2. The method of claim 1, wherein the introgressing comprises:
   a) assaying pepper plants for the presence of at least one allele of a marker genetically linked to a chromosomal interval that confers resistance to Powdery Mildew;
   b) selecting at least a first pepper plant comprising the allele and the chromosomal interval that confers resistance to Powdery Mildew, wherein the chromosomal interval maps to a position between the sequence represented by marker NE0240275 and marker NE0240958, or the chromosomal interval maps to a position between the sequence represented by marker NE0240275 and marker NE0237348, which map to approximately 21.56 cM and 45.27 cM, respectively, on the genetic map of the linkage group termed pepper chromosome 4; and
   c) self-pollinating the first pepper plant or cross pollinating the first pepper plant with a second pepper plant to produce at least a first progeny pepper plant comprising the chromosomal interval.

3. The method of claim 2, wherein selecting the first pepper plant further comprises selecting the plant based on the presence of a plurality of marker alleles that map to a position between the sequences represented by markers NE0240275 and NE0240958, or the chromosomal interval maps to a position between the sequence represented by marker NE0240275 and marker NE0237348, which map to approximately 21.56 cM and 45.27 cM, respectively, on the genetic map of the linkage group termed pepper chromosome 4.

4. The method of claim 2, further comprising the step of
   d) selecting a progeny plant comprising the allele which is linked with resistance to Powdery Mildew and self-pollinating, backcrossing with a recurrent parent or cross-pollinating the progeny plant with a third pepper plant to produce additional progeny plants.

5. The method of claim 4, wherein the method further comprises repeating step (d) about 2-10 times.

6. The method of claim 3, wherein the alleles are from markers selected from the group consisting of NE0236790, NE0238624, NE0240275, NE0238899, NE0238734, NE0240256, NE0237985, NE0239638, NE0239147, NE0240589, and NE0237975.

7. The method of claim 3, wherein the alleles are from markers selected from the group consisting of NCANN005704058, NCANN005704056, and NCANN005704052.

8. The method of claim 2, wherein assaying the pepper plants comprises PCR, single strand conformational polymorphism analysis, denaturing gradient gel electrophoresis, cleavage fragment length polymorphism analysis, TAQ-MAN assay, and/or DNA sequencing.

9. The method of claim 2, wherein the marker is one or more markers selected from the group consisting of NE0236790, NE0237985, NE0239147, NE0240438, and NE0237348.

10. The method of claim 2, wherein the marker is NE0236790 or NE0237985.

11. The method of claim 2, wherein the marker is one or more markers selected from the group consisting of NCANN005704058, NCANN005704056, and NCANN005704052.

12. The method of claim 2, wherein the chromosomal interval that confers resistance to Powdery Mildew confers a reduction of *Leveillula taurica* sporulation of at least, or greater than, 25%, relative to a nonresistant control pepper line.

13. The method of claim 3, wherein the alleles are from markers selected from the group consisting of NCANN005704049, NE0239291, NE0235654, NE0238449, NE0240786, NE0239990, NE0231151, NE0240438, NE0237121, NE0238426, NE0235272, NE0237901, NE0237351, and NE0241057.

* * * * *